(12) United States Patent
Sakaguchi et al.

(10) Patent No.: US 10,117,662 B2
(45) Date of Patent: Nov. 6, 2018

(54) MEDICAL MANIPULATOR

(71) Applicant: Karl Storz SE & Co. KG, Tuttlingen (DE)

(72) Inventors: Yuuki Sakaguchi, Fujinomiya (JP); Shinji Ishida, Fujinomiya (JP)

(73) Assignee: Karl Storz SE & Co. KG, Tuttlingen (DE)

( * ) Notice: Subject to any disclaimer, the term of this patent is extended or adjusted under 35 U.S.C. 154(b) by 358 days.

(21) Appl. No.: 14/872,552

(22) Filed: Oct. 1, 2015

(65) Prior Publication Data

US 2016/0022299 A1 Jan. 28, 2016

Related U.S. Application Data

(63) Continuation of application No. PCT/JP2013/060124, filed on Apr. 2, 2013.

(51) Int. Cl.
*A61B 17/29* (2006.01)
*A61B 18/14* (2006.01)
(Continued)

(52) U.S. Cl.
CPC .......... *A61B 17/29* (2013.01); *A61B 17/2909* (2013.01); *A61B 18/1445* (2013.01);
(Continued)

(58) Field of Classification Search
CPC .......... A61B 17/29; A61B 2017/00199; A61B 2017/003; A61B 2017/00314; A61B 2017/00398; A61B 2017/0046; A61B 2017/00464; A61B 2017/00473; A61B 2017/2903; A61B 2017/2927; A61B 2018/00178; A61B 2018/0094; A61B 2018/00952
(Continued)

(56) References Cited

U.S. PATENT DOCUMENTS 3,801,766 A * 4/1974 Morrison, Jr. ..... A61B 18/1402
200/275
4,034,761 A * 7/1977 Prater ................ A61B 18/1402
200/505
(Continued)

FOREIGN PATENT DOCUMENTS

JP 36030730 Y1 11/1961
JP 2004329624 A 11/2004
(Continued)

OTHER PUBLICATIONS

European Search Report Application No. 13881210.2 Completed: Jul. 21, 2016 dated Jul. 28, 2016 6 Pages.
(Continued)

*Primary Examiner* — Michael Peffley
(74) *Attorney, Agent, or Firm* — Whitmyer IP Group LLC

(57) ABSTRACT

A switch mechanism for a medical manipulator, the switch mechanism including a moveable switching operation part, moving-side contacts provided to the switching operation part, and fixed-side contacts capable of contacting the moving-side contacts. At least the electrical-contact sections of the moving-side contacts and of the fixed-side contacts are formed from a corrosion-resistant material.

16 Claims, 15 Drawing Sheets

(51) Int. Cl.
  *A61B 17/00* (2006.01)
  *A61B 18/00* (2006.01)
(52) U.S. Cl.
  CPC . *A61B 2017/003* (2013.01); *A61B 2017/0046* (2013.01); *A61B 2017/00199* (2013.01); *A61B 2017/00314* (2013.01); *A61B 2017/00398* (2013.01); *A61B 2017/00477* (2013.01); *A61B 2017/2903* (2013.01); *A61B 2017/2927* (2013.01); *A61B 2018/00178* (2013.01); *A61B 2018/00952* (2013.01)
(58) Field of Classification Search
  USPC ................................................ 606/32–50
  See application file for complete search history.

(56) References Cited

U.S. PATENT DOCUMENTS

| | | | | |
|---|---|---|---|---|
| 4,427,006 A | * | 1/1984 | Nottke | A61B 18/1402 200/302.1 |
| 4,443,935 A | * | 4/1984 | Zamba | A61B 18/1402 29/622 |
| 4,463,759 A | * | 8/1984 | Garito | A61B 18/12 307/117 |
| 4,548,207 A | * | 10/1985 | Reimels | A61B 18/1402 206/363 |
| 4,918,264 A | | 4/1990 | Yamamoto et al. | |
| 5,426,275 A | | 6/1995 | Maeda et al. | |
| 5,610,379 A | * | 3/1997 | Muz | A61B 18/1402 200/302.3 |
| 2008/0215046 A1 | * | 9/2008 | Messing | A61B 18/00 606/41 |
| 2009/0182327 A1 | | 7/2009 | Unger | |

FOREIGN PATENT DOCUMENTS

| | | |
|---|---|---|
| JP | 2008104854 A | 5/2008 |
| JP | 2009537957 A | 10/2009 |
| JP | 2011177430 A | 9/2011 |
| WO | 2010150618 A1 | 12/2010 |

OTHER PUBLICATIONS

International Search Report Application No. PCT/JP2013/060124 Completed: Jun. 3, 2013; dated Jun. 11, 2013 2 pages.

* cited by examiner

MEDICAL MANIPULATOR

FIELD OF THE INVENTION

The present invention relates to a medical manipulator equipped with a switch mechanism.

BACKGROUND OF THE INVENTION

In an endoscopic surgical operation (also referred to as "laparoscopic surgery"), one or a plurality of holes are punctured in the abdomen or the like of a patient, and trocars (cylindrical instruments) are inserted through the holes. Thereafter, a laparoscope (camera) and a plurality of forceps are inserted into the body cavity via the one or more trocars. Grippers for gripping biological tissue, scissors, or blades of an electrosurgical scalpel are mounted to the distal end of the forceps as an end effector.

If the laparoscope and the forceps are inserted into the body cavity, an operator operates the forceps while viewing a state of the inner portion of the abdominal cavity, which is shown on a monitor that is connected to the laparoscope. Since the surgical procedure does not require a laparotomy, the burden on the patient is reduced, which reduces the number of days for postoperative recovery and leaving the hospital. For this reason, the fields that such an operative method can be applied to are expected to expand.

Other than typical forceps that are not provided with joints at distal end portions thereof, as forceps that are inserted through a trocar, forceps referred to as a medical manipulator have been developed that are provided with joints at distal end portions and which can carry out a rolling operation or a tilting operation of an end effector (for example, refer to Japanese Patent No. 4391762). In accordance with such a medical manipulator, a high degree of operational freedom is facilitated in the body cavity, manual procedures are made easy, and thus there are a large number of medical cases to which the medical manipulator may be applied.

Further, with the aim of improving operability and facilitating manipulation, a medical manipulator has been proposed that carries out a portion or all of the operations of a distal end working unit by a drive source (motor) (see, for example, Japanese Laid-Open Patent Publication No. 2008-104854). In this type of medical manipulator, a switch operating member is provided on the handle. When the switch operating member is operated, a drive source is driven corresponding to the operating state of the switch operating member, and a distal end working unit is operated accordingly.

SUMMARY OF THE INVENTION

Incidentally, after use of the medical manipulator, normally, a sterilization process is performed for cleaning and preparation for a next use of the medical manipulator. In the case of sterilization in which steam is used (autoclave sterilization, etc.), the switch mechanism including a switch operating member is exposed to water vapor. Accordingly, concerning the switch structure provided in the medical manipulator, it is desirable for the structure to be capable of withstanding the sterilization treatment in which steam is used.

The present invention has been devised while taking into consideration the aforementioned problems, and has the object of providing a medical manipulator equipped with a switch mechanism that can withstand a sterilization treatment in which steam is used.

For achieving the aforementioned object, the present invention is characterized by a medical manipulator equipped with a switch mechanism, in which the switch mechanism includes a movable switch operating member, a movable-side contact portion disposed on the switch operating member, and a fixed-side contact portion, which is capable of abutting against the movable-side contact portion, and wherein at least electrical contact portions of the movable-side contact portion and the fixed-side contact portion are formed from a corrosion-resistant material.

According to the above configuration, in the switch mechanism, at least the electrical contact portions of the movable-side contact portion and the fixed-side contact portion are constituted from a corrosion-resistant material. For this reason, even if subjected to a sterilization treatment (autoclave sterilization, etc.) in which steam is used, it is unlikely for an oxide layer to be formed on the movable-side contact portion and the fixed-side contact portion, and conductivity can be maintained. Consequently, according to the present invention, a medical manipulator can be offered, which is equipped with a switch mechanism that can withstand a sterilization treatment in which steam is used.

In this case, at a time of contact, the movable-side contact portion and the fixed-side contact portion rub against each other at contact locations therebetween. In accordance with such a configuration, even if an oxide layer is generated on each of contact points between the movable-side contact portion and the first and second fixed-side contact portions, the movable-side contact portion and the fixed-side contact portion rub against each other, and at the portions subjected to such mutual rubbing, an effect (refreshing effect) by which the electrical contact portions are activated can be obtained. Consequently, even if an oxide layer occurs or foreign matter is deposited or adhered thereon as a result of performing a sterilization treatment using steam, the electrical connection can suitably be assured as a result of the refreshing effect.

When the fixed-side contact portion comes into contact with the movable-side contact portion, a contact region of the fixed-side contact portion with the movable-side contact portion may be capable of being displaced elastically. According to such a structure, when the movable-side contact portion is placed in contact with the fixed-side contact portion, the fixed-side contact portion is pressed and displaced elastically by the movable-side contact portion, and at this time, mutual rubbing takes place at the contact regions. Thus, with a simple structure, the aforementioned refreshing effect can be obtained.

The fixed-side contact portion may be constituted as an elastically deformable plate-shaped body. With this configuration, in the fixed-side contact portion, since the elastic displacement function and the conductive element are integrated as a single member, the structure is simplified.

Further, in the medical manipulator, when the movable-side contact portion comes into contact with the fixed-side contact portion, a contact region of the movable-side contact portion with the fixed-side contact portion may be capable of being displaced elastically. According to such a structure, when the movable-side contact portion is placed in contact with the fixed-side contact portion, the movable-side contact portion is pressed and displaced elastically by the fixed-side contact portion, and at this time, mutual rubbing takes place at the contact regions. Thus, with a simple structure, the aforementioned refreshing effect can be obtained.

The movable-side contact portion may be constituted as an elastically deformable plate-shaped body. With this configuration, in the movable-side contact portion, since the spring element and the electrically conductive element are integrated into a single member, the structure is simplified.

In the medical manipulator, the fixed-side contact portion may include a first fixed-side contact portion that abuts against the movable-side contact portion when the switch operating member is operated in a first direction from a neutral position, and a second fixed-side contact portion that abuts against the movable-side contact portion when the switch operating member is operated in a second direction opposite to the first direction from the neutral position. According to this configuration, since a two-way operation can be manipulated by switching the contact state between the movable-side contact portion, the first fixed-side contact portion, and the second fixed-side contact portion, the configuration serves as a suitable switching mechanism for the medical manipulator.

The medical manipulator may contain a manipulator main body including a handle, and a drive unit that is capable of attachment and detachment with respect to the handle, and which includes a drive source. In this case, the switch mechanism may be disposed in the handle. According to this structure, since the drive source is provided on the side of the drive unit, there is no need to provide electronic devices, which are susceptible to moisture, in the manipulator main body. Accordingly, a sterilization treatment in which steam is used can suitably be performed on the manipulator main body.

DETAILED DESCRIPTION OF THE INVENTION

Hereinafter, a preferred embodiment of a medical manipulator according to the present invention will be described in detail below with reference to the accompanying drawings.

Figure 1:
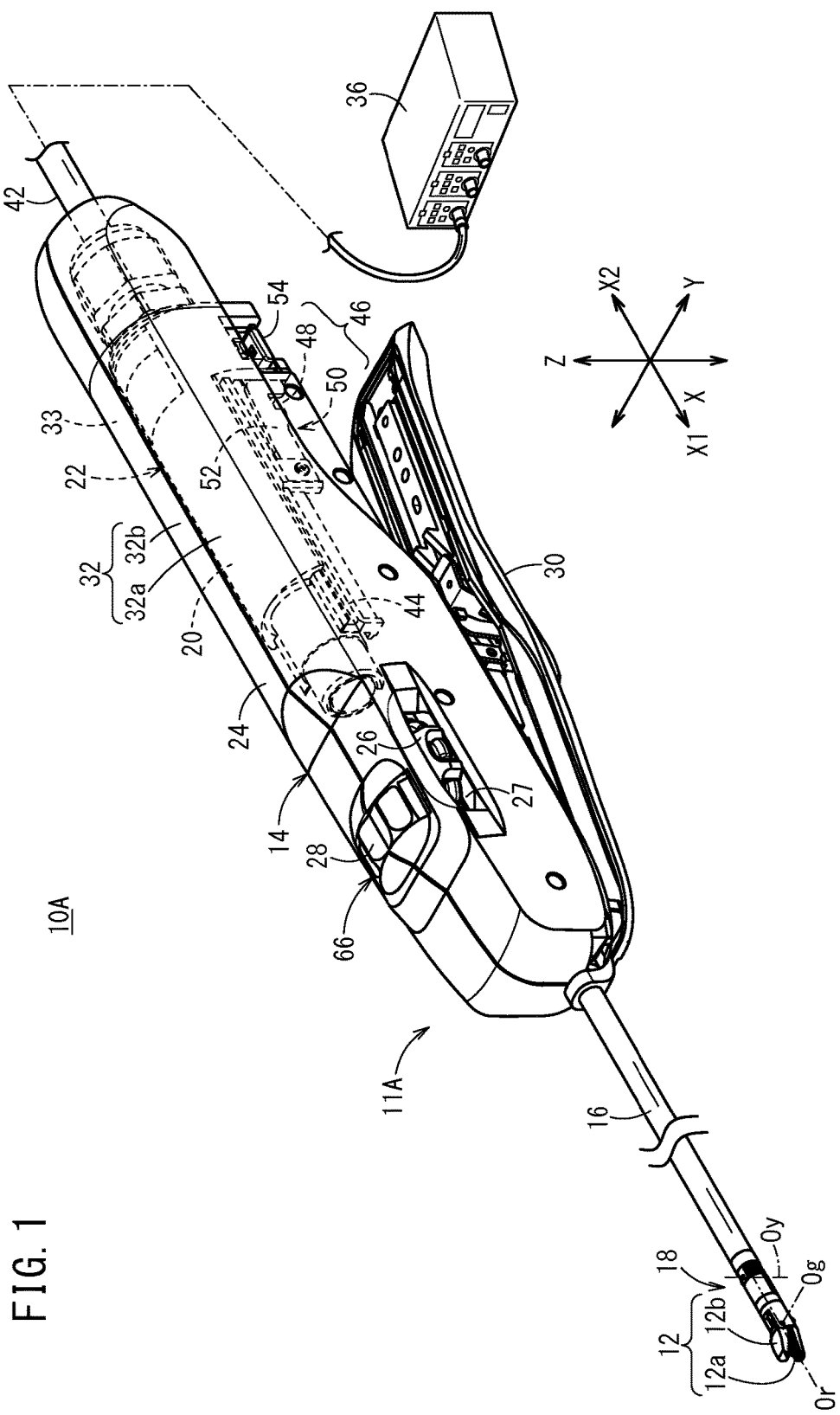
FIG. 1 is a perspective view with partial omission of a medical manipulator according to an embodiment of the present invention.

FIG. 1 is a perspective view with partial omission of a medical manipulator 10A (hereinafter referred to in abbreviated form as a "manipulator 10A") according to an embodiment of the present invention. The manipulator 10A is a medical device that grasps a needle, a thread, or a part of the living body or touches the living body using a gripper 12 (end effector) provided at the distal end thereof, and carries out a predetermined treatment.

The manipulator 10A comprises a handle 14 on which a plurality of input operating members are provided, a shaft 16 that extends from the handle 14, a distal end working unit 18 disposed on a distal end of the shaft 16 including a gripper 12, and a drive unit 22 in which a motor 20 (drive source) is provided for driving the distal end working unit 18, and which is capable of attachment and detachment to and from the handle 14. A manipulator main body 11A is made up from the handle 14, the shaft 16, and the distal end working unit 18.

In the following description, in relation to the manipulator 10A and the constituent elements thereof, in the drawings, the X direction indicates a forward and rearward longitudinal direction, the Y direction indicates a left and right lateral direction, and the Z direction indicates an up and down vertical direction. In particular, the X1 direction is a forward direction, and the X2 direction is a rearward direction.

With the manipulator 10A according to the present embodiment, the manipulator main body 11A and the drive unit 22 can be attached and detached to and from each other. In a state in which the drive unit 22 is taken out from the manipulator main body 11A, the driving force from the motor 20 is not transmitted to the distal end working unit 18. On the other hand, in a state in which the drive unit 22 is mounted on the handle 14, when the motor 20 is driven, the driving force of the motor 20 is transmitted to the distal end working unit 18.

The manipulator 10A shown in FIG. 1 is constituted as a needle driver that is capable of grasping a medical needle (a curved needle or the like) with the gripper 12 disposed on the distal end thereof. The gripper 12 is a portion that carries out a surgical treatment, and in the illustrated example, the gripper 12 includes first and second gripper members 12a, 12b, and is configured to carry out opening and closing operations on the basis of a predetermined opening and closing operation axis Og. In the illustrated example, although concerning the gripper 12, a case has been described in which the first gripper member 12a is constituted as a fixed member and the second gripper member 12b is constituted as a movable member, both of the gripper members 12a, 12b may be constituted as movable members.

The posture of the distal end working unit 18 including the gripper 12 can be changed at a plurality of degrees of freedom with respect to the shaft 16. In the present embodiment, the distal end working unit 18 can carry out a "tilting operation" (swinging operation) in which the distal end working unit 18 is operated to tilt in left and right (transverse or lateral) directions with respect to an axis of the shaft 16 about a tilt axis Oy, and a "rolling operation" in which the distal end working unit 18 is rotated about the axial line (roll axis Or) in the longitudinal direction of the distal end working unit 18. The tilt axis Oy is not limited to being set in the vertical direction, and the tilt axis Oy may be set in a different direction that intersects the axis of the shaft 16.

The shaft 16 is an oblong small diameter tubular member that connects the handle 14 and the distal end working unit 18. In FIG. 1, a portion of the shaft 16 is omitted from illustration, and the shaft is rendered shorter than it actually is. A plurality of members configured to make up a power transmission mechanism are inserted through and arranged in a hollow portion of the shaft 16. Such a power transmission mechanism transmits, from the handle 14 to the distal end working unit 18, power that is necessary for carrying out the opening and closing operation of the gripper 12, and the rolling operation and the tilting operation of the distal end working unit 18.

A structure may be provided in which one or a plurality of joints are provided at an intermediate location in the longitudinal direction of the shaft 16 to enable the tilting operation by the joints. Further, a structure may be provided in which the rolling operation is enabled at the proximal end portion of the shaft 16, or at an intermediate location in the longitudinal direction of the shaft 16.

The handle 14 is a portion that is gripped by an operator during use of the manipulator 10A, and by input operating members (in the present embodiment, a later described tilt wheel 26, a rolling switch 28, and a lever 30) being touched and operated by a finger, drives the distal end working unit 18 that is connected to the distal end of the shaft 16.

The handle 14 comprises a body portion 24 that is connected to a proximal end of the shaft 16, the tilt wheel 26 constituting a tilt operating unit that is provided on the body portion 24, the rolling switch 28 (switch operating member) constituting a rolling operating unit that is provided on the body portion 24, and the lever 30 constituting an opening and closing operating unit that is provided on the body portion 24.

The body portion 24 makes up a part that is gripped by a user when the manipulator 10A is used. In the present embodiment, the body portion 24 is constituted in the form of a stick that extends over a certain length in the axial direction of the shaft 16. The body portion 24 includes a casing 32 made up from a left cover 32a and a right cover 32b, with frames, drive components (pulleys, gears, wires, etc.) or the like being arranged in the interior of the casing 32. For insertion and installation of the drive unit 22 in the interior of the casing 32 from the rear side, a rearwardly open installation hole 33 is formed.

The tilt wheel 26 for carrying out a tilting operation of the distal end working unit 18 is disposed near the center in the longitudinal direction of the body portion 24, and is rotatable about the vertically oriented axis of the handle 14. The tilt wheel 26 is constituted as a manual operating member, such that the tilt wheel 26 partially protrudes from openings 27 provided on left and right sides of the casing 32.

When the tilt wheel 26 is operated by being rotated, the operating force applied thereto is transmitted mechanically to the distal end working unit 18 through a tilting operation power transmission system, which is disposed internally in the handle 14 and the shaft 16, whereupon the distal end working unit 18 is tilted about an axis (tilt axis Oy) in a non-parallel direction with respect to the axis of the shaft 16. More specifically, when the tilt wheel 26 is rotated clockwise as viewed in plan, the distal end working unit 18 is tilted in a rightward direction about the handle 14, whereas when the tilt wheel 26 is rotated counterclockwise as viewed in plan, the distal end working unit 18 is tilted in a leftward direction about the handle 14.

With the manipulator 10A of the illustrated example, the rolling switch 28 for carrying out a rolling operation of the distal end working unit 18 is disposed on an upper portion in the vicinity of the distal end of the body portion 24. In the present embodiment, the rolling switch 28 is constituted as an electrical manipulating portion, which supplies an operating command to the motor 20 through a controller 36. Because the rolling switch 28 is an electrical switch, the rolling switch 28 is not limited to the location shown in FIG. 1, but can be arranged in a different location of the handle 14.

In a state in which the drive unit 22 is mounted in the handle 14, and the power source of the controller 36 is turned on, when the rolling switch 28 is operated and moved, the operating state (position) of the rolling switch 28 is detected by the controller 36, the motor 20 is driven under the controlling action of the controller 36, and by the driving force of the motor 20 being transmitted to the distal end working unit 18, the distal end working unit 18 is rotated about the longitudinal axis (roll axis Or) of the distal end working unit 18.

A lever 30 for performing an opening and closing operation of the gripper 12 is disposed on a lower part of the body portion 24, and is swingably mounted upward and downward about the distal end side thereof which serves as a support point. According to the present embodiment, the lever 30 is constructed as a manual operating member, in which an opening and closing operation of the gripper 12 is carried out by mechanically transmitting to the gripper 12 of the distal end working unit 18 an operating force applied with respect to the lever 30. More specifically, a structure is provided in which the gripper 12 is opened when the lever 30 is opened, and the gripper 12 is closed when the lever 30 is closed.

As shown in FIG. 1, the drive unit 22 of the manipulator 10A is used in a condition of being connected to the controller 36 through a cable 42. The controller 36 controls the supply of power and driving or the like of the motor 20, and receives electrical power from an external power source. In a state in which the drive unit 22 is mounted on the handle 14, when the rolling switch 28 is operated, the controller 36 controls driving of the motor 20 in response to operation thereof. The rotation of the motor 20 may be detected, and the motor 20 may be feedback controlled through the controller 36.

The form of use can be one in which, concerning the manipulator 10A that is constructed in the foregoing manner, the manipulator main body 11A can be discarded after being used a predetermined number of times, whereas the drive unit 22 can be used repeatedly many times by changing the manipulator main body 11A that is connected to the drive unit 22.

Figure 2:
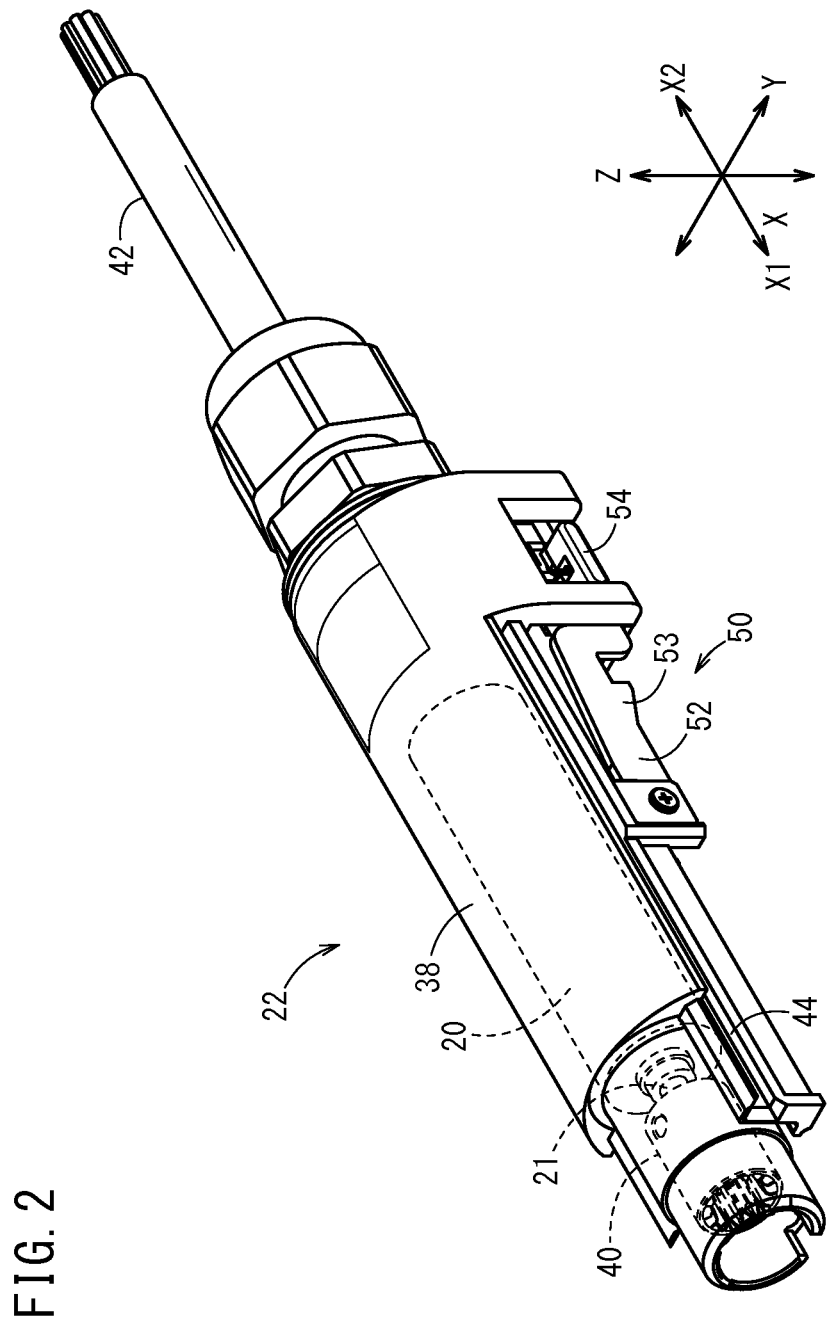
FIG. 2 is a perspective view of a drive unit.

FIG. 2 is a perspective view of the drive unit 22. The drive unit 22 includes a housing 38, the motor 20 (drive source) disposed inside the housing 38, and a drive coupling 40 (drive member) that is fixed to an output shaft 21 of the motor 20. The cable 42 including power lines and signal lines is connected to the proximal end side of the drive unit 22.

In a state in which the drive unit 22 is attached to the handle 14 (see FIG. 1), the drive coupling 40, which is fixed to the output shaft 21 of the motor 20, is fitted (enmeshed) with a non-illustrated driven coupling (driven member) disposed on the side of the handle 14. In this state in which the drive coupling 40 and the driven coupling are fitted together, when the motor 20 is rotated, the rotary driving force of the motor 20 is transmitted to the side of the handle 14 through the drive coupling 40 and the driven coupling.

In the handle 14, guide rails (not shown) that extend along a longitudinal (forward and rearward) direction of the handle 14, are provided on both left and right sides on an inside surface of the casing 32. As shown in FIG. 2, groove-shaped guide receiving members 44 that extend in the longitudinal direction of the drive unit 22 are disposed on side surfaces on both left and right sides of the housing 38.

When the drive unit 22 is attached with respect to the handle 14, under a guiding action of the guide rails and the guide receiving members 44, the drive unit 22 can be moved smoothly relative to the handle 14. Consequently, the drive unit 22 can be mounted easily and reliably at an accurate positional relationship with respect to the handle 14.

As shown in FIG. 1, in the drive unit 22, a lock mechanism 46 is provided that restricts the drive unit 22 so as not to become detached from the handle 14, in a state in which the drive unit 22 has been attached to the handle 14. The lock mechanism 46 of the present illustrated example includes an engagement member 48 (see FIG. 3) disposed on the handle 14, and a lever device 50 disposed on the drive unit 22.

As shown in FIG. 2, the lever device 50 includes a lever member 52, an operating tab 54, and a lever biasing member (not shown). The lever member 52 is swingable with respect to the housing 38, and is equipped with an engagement pawl 53. The operating tab 54 is disposed on a proximal end of the lever member 52. The lever biasing member biases the lever member 52 elastically in a direction in which the engagement pawl 53 projects (a downward direction as shown in the illustrated example).

When the drive unit 22 is attached to the handle 14, the engagement pawl 53 disposed on the lever member 52 engages with the engagement member 48 provided inside the handle 14, whereby the drive unit 22 is prevented from becoming detached and separating away from the handle 14. On the other hand, by releasing the engagement between the engagement member 48 and the engagement pawl 53 of the lever member 52, the drive unit 22 is capable of being detached from the handle 14.

In the manipulator 10A, there is further provided an electrical connection mechanism that electrically connects the handle 14 and the drive unit 22 accompanying attachment of the drive unit 22 to the handle 14. The electrical connection mechanism includes handle-side terminal members 60 (see FIG. 3) disposed on the handle 14, and unit-side terminal members 62 (see FIG. 4) disposed on the drive unit 22.

The handle-side terminal members 60 and the unit-side terminal members 62 are made from a conductive material. The handle-side terminal members 60 and the unit-side terminal members 62 preferably are constituted from a corrosion-resistant material, for example, stainless steel, titanium, a titanium alloy, etc.

Figure 3:
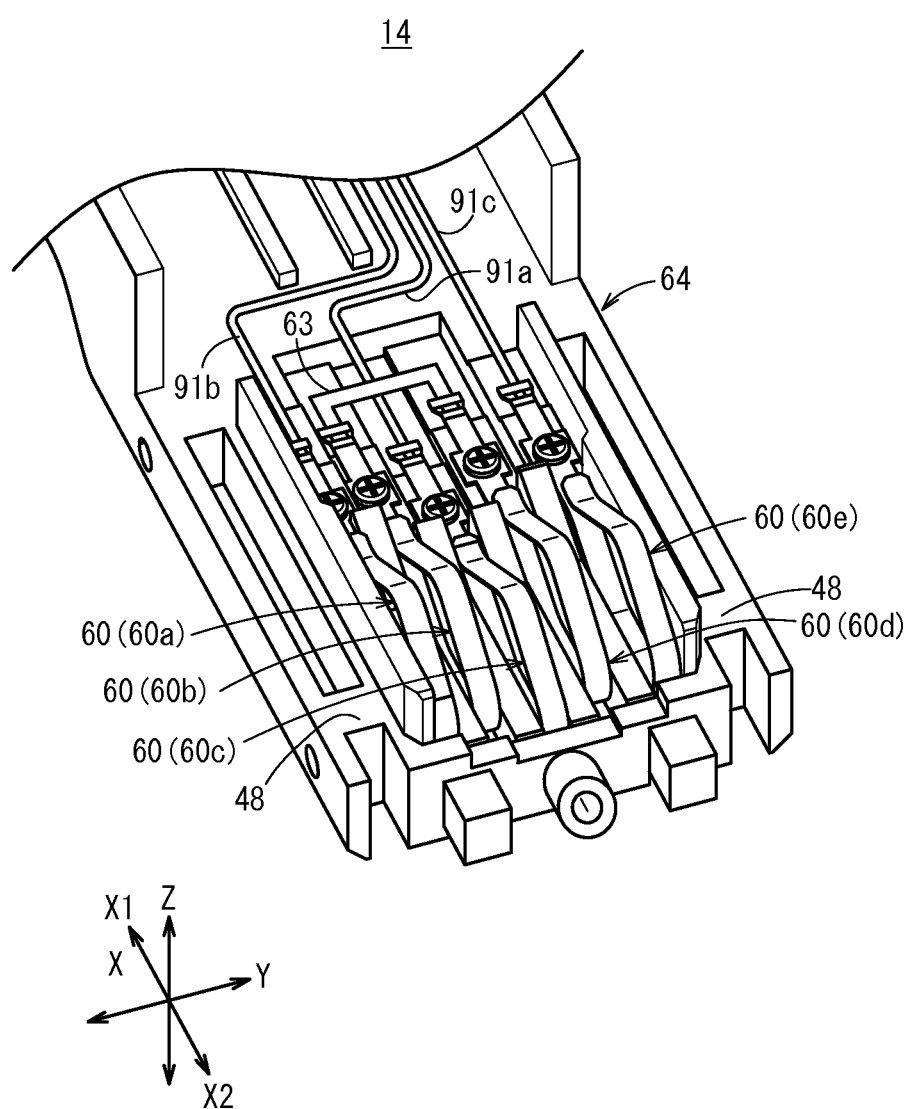
FIG. 3 is a perspective view showing the arrangement of a handle-side terminal member.

As shown in FIG. 3, in the handle 14, a unit holder 64 is provided that extends in forward and rearward directions of the handle 14. On an upper surface of a proximal end side of the unit holder 64, plural handle-side terminal members 60 are provided. In the present illustrated example, five handle-side terminal members 60a to 60e are arranged at intervals in the widthwise direction (lateral direction: Y direction) of the handle 14.

Figure 5:
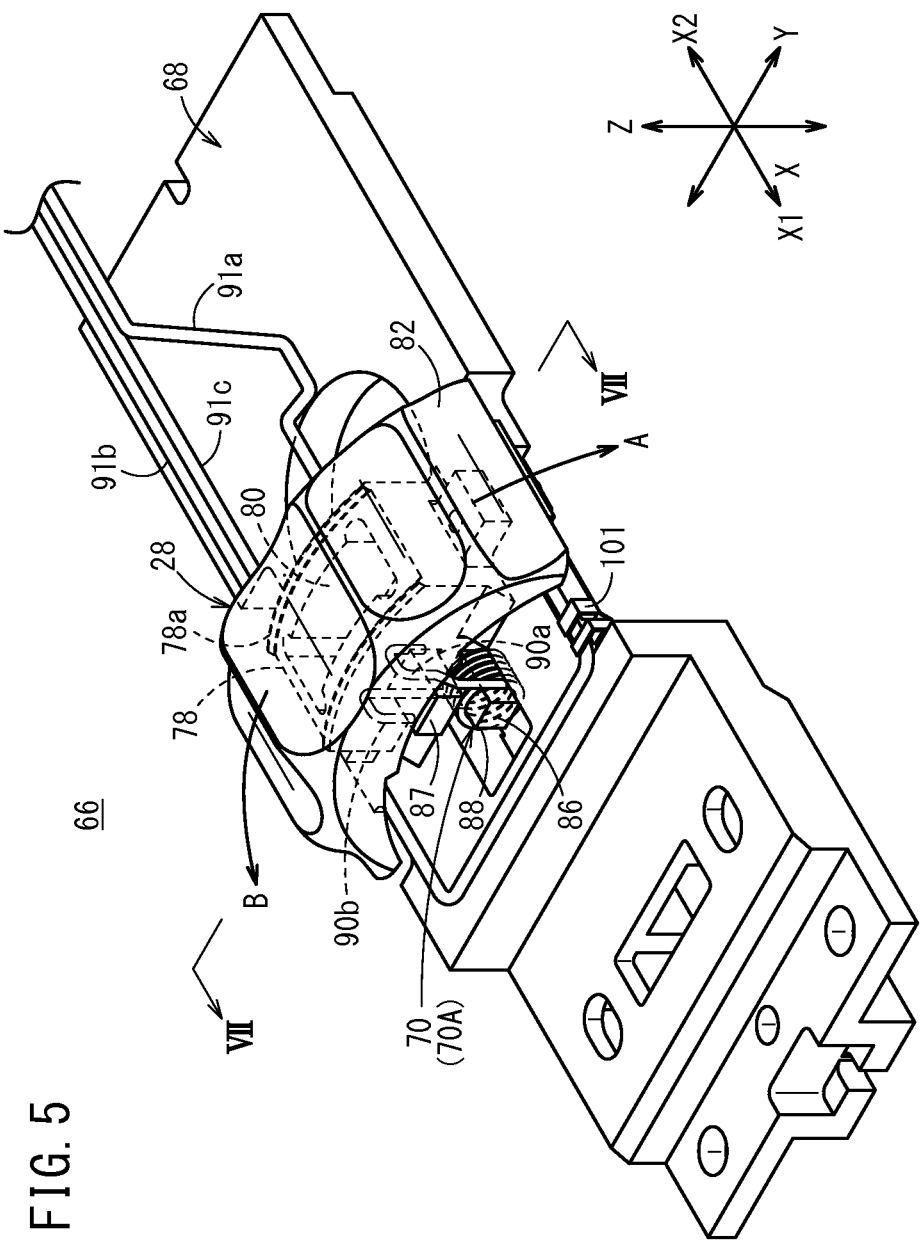
FIG. 5 is a perspective view of a switch mechanism in the medical manipulator illustrated in FIG. 1.
Figure 6:
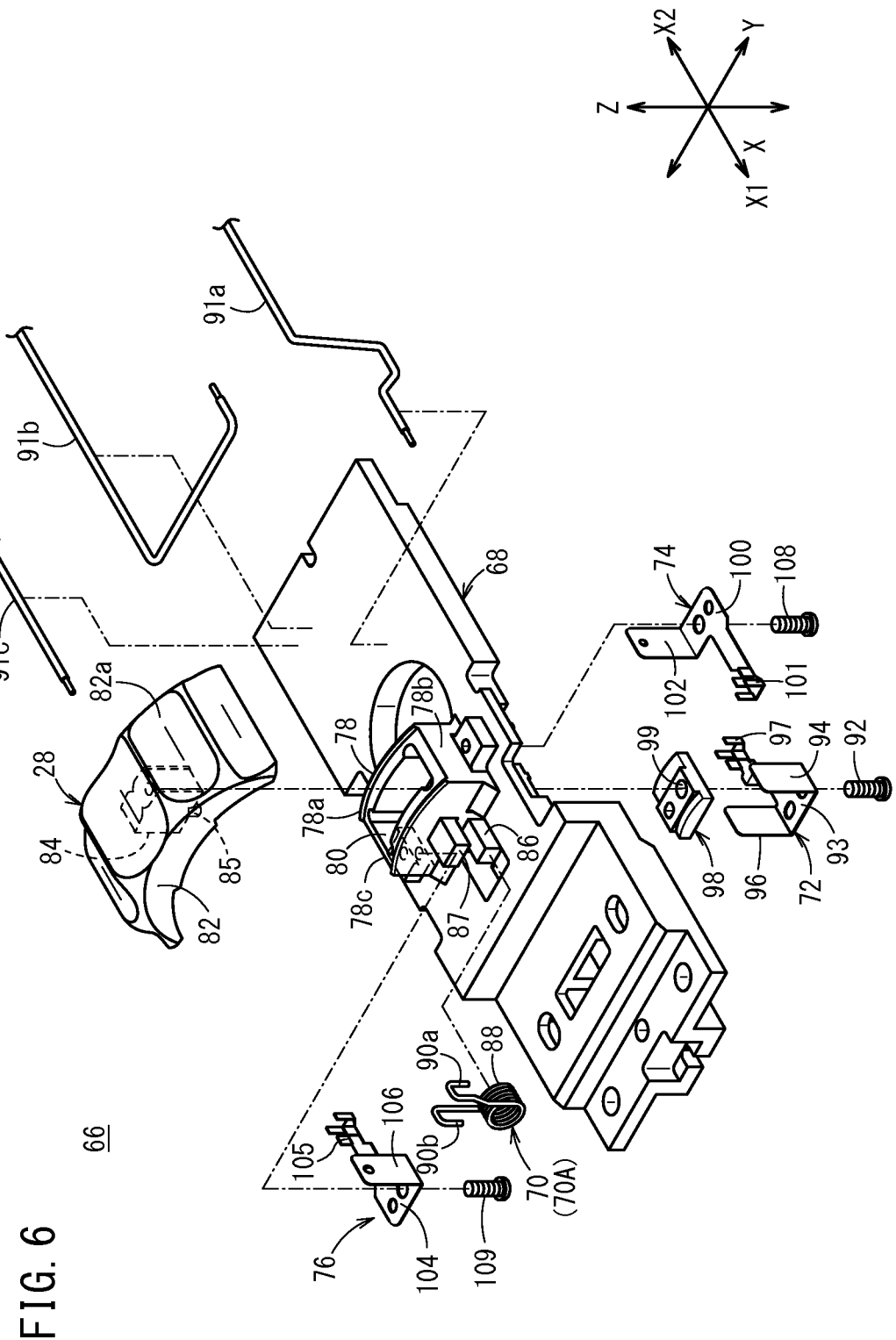
FIG. 6 is an exploded perspective view of the switch mechanism shown in FIG. 5.

The central handle-side terminal member 60c and the two handle-side terminal members 60a, 60e on outermost sides thereof are connected, through respective lead wires 91a to 91c connected thereto, to a switch mechanism 66 including the rolling switch 28 (see FIGS. 1, 5, and 6). The handle-side terminal members 60a, 60c, 60e function as switch terminals (operation terminals) for detecting the operating state of the rolling switch 28.

The other two handle-side terminal members 60b, 60d are electrically connected via a short-circuiting member 63. The handle-side terminal members 60b, 60d function as detection terminals for detecting whether or not the drive unit 22 has been attached with respect to the handle 14.

In the present illustrated example, among the five handle-side terminal members 60a to 60e, the switch terminals and the detection terminals are arranged alternately one by one. However, the manner of arrangement thereof is not limited, and the switch terminals and the detection terminals may be arranged in any manner.

Figure 4:
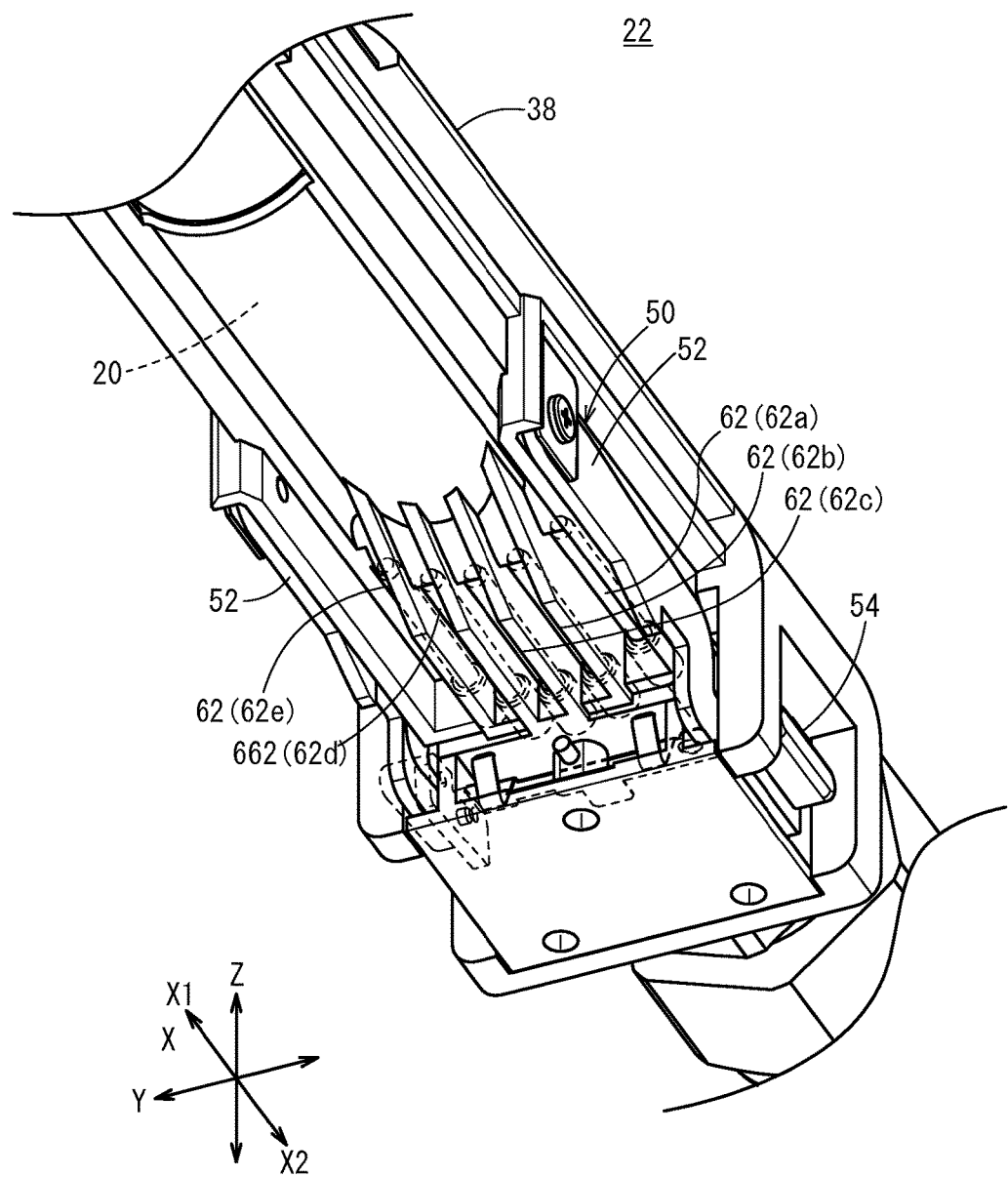
FIG. 4 is a perspective view, as seen obliquely from below, of the drive unit.

FIG. 4 is a perspective view as seen obliquely from below the drive unit 22. In the present embodiment, five unit-side terminal members 62a to 62e are disposed mutually in parallel and with intervals therebetween in the circumferential direction of the motor 20. The respective unit-side terminal members 62 are shaped in the form of elongate narrow pins, with the longitudinal directions thereof being arranged along the longitudinal direction of the drive unit 22. The respective unit-side terminal members 62 may be plate-shaped.

In a state in which the drive unit 22 is mounted on the handle 14, the central unit-side terminal member 62c and the outermost unit-side terminal members 62a, 62e are in contact with the central handle-side terminal member 60c and the outermost handle-side terminal members 60a, 60e (switch terminals) provided on the handle 14, whereas the remaining two unit-side terminal members 62b, 62d are in contact with the two handle-side terminal members 60b, 60d (detection terminals) provided on the handle 14.

Figure 7:
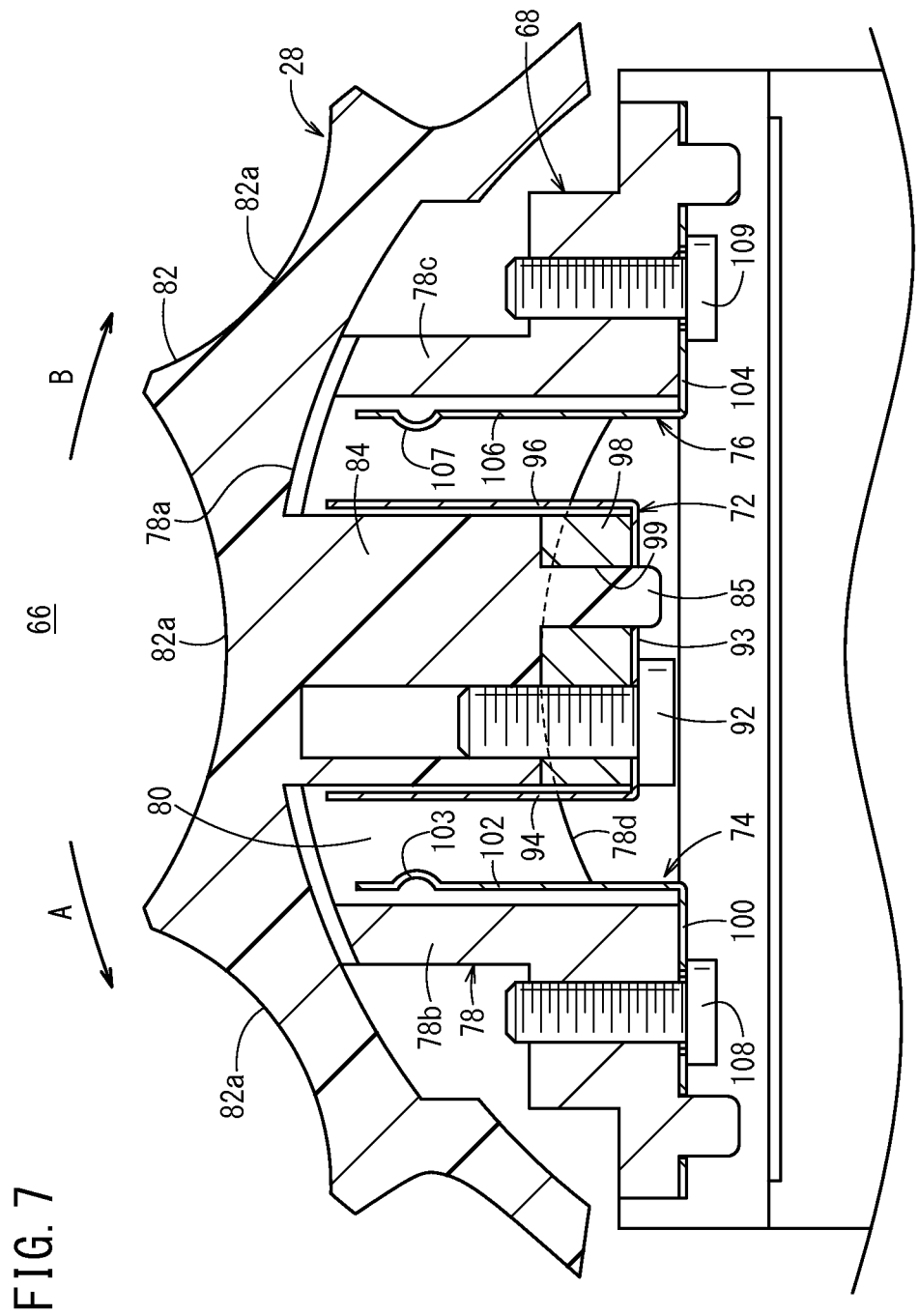
FIG. 7 is a cross-sectional view of the switch mechanism taken along line VII-VII of FIG. 5.

FIG. 5 is a perspective view showing a switch mechanism 66 including the rolling switch 28. FIG. 6 is an exploded perspective view of the switch mechanism 66. FIG. 7 is a transverse cross-sectional view of the switch mechanism 66 taken along line VII-VII of FIG. 5. As shown in FIGS. 5 through 7, the switch mechanism 66 includes a switch frame 68, the rolling switch 28 that makes up the switch operating member, a biasing member 70, a movable-side terminal member 72, a first fixed-side terminal member 74, and a second fixed-side terminal member 76.

The switch frame 68 is fixed to a non-illustrated frame disposed in the interior of a casing of the handle 14. The switch frame 68 swingably supports the rolling switch 28. On the switch frame 68 of the present illustrated example, a switch pedestal 78, which swingably supports the rolling switch 28, is formed in an upwardly projecting manner. The switch pedestal 78 includes an arcuate slide surface 78a. An insertion hole 80 that penetrates in a vertical direction is disposed in the switch pedestal 78.

The rolling switch 28 is a portion that is operated by a finger of the user of the manipulator 10A. The rolling switch 28 of the present illustrated example includes an operating element 82 that is constituted in an arcuate shape, and a projecting member 84 that projects from a central rear side of the operating element 82. On an outer peripheral part of the operating element 82, a plurality (three) of arcuate recesses 82a are provided to which the finger can easily be applied.

Figure 9:
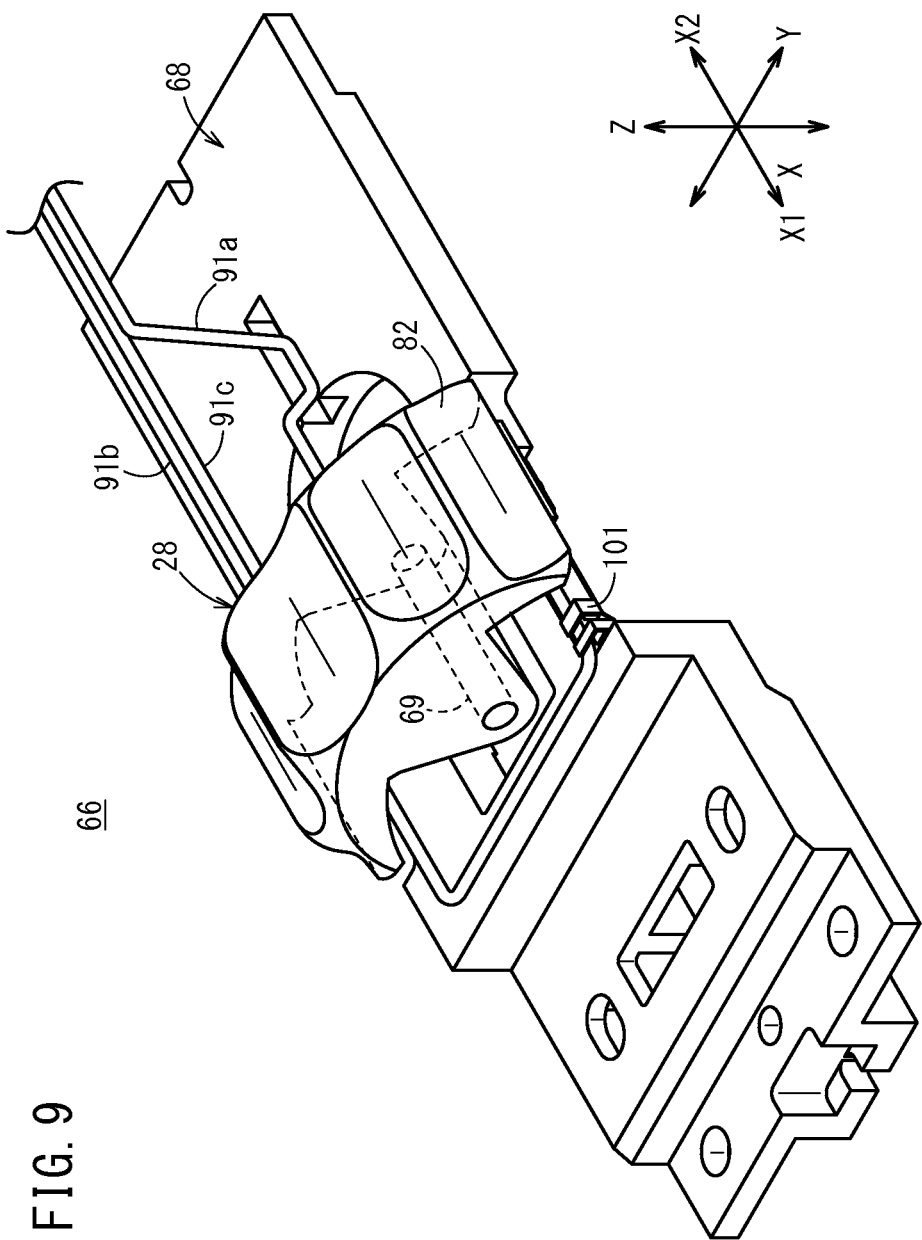
FIG. 9 is a perspective view of the switch mechanism including a modification of the rolling switch.

A lower surface of the operating element 82 is supported slidably by a slide surface 78a of the switch pedestal 78. Consequently, the rolling switch 28 can be swung in the A direction and the B direction shown in FIG. 7. A pivotal center of the rolling switch 28 is coincident with the center of curvature of the arcuately shaped slide surface 78a. As shown in FIG. 9, in a modification of the rolling switch 28, the rolling switch 28 may be supported through a rotating shaft 69 on the switch frame 68, and thereby arranged in a swingable manner. Alternatively, according to another modification of the rolling switch 28, the rolling switch 28 may be arranged so as to be displaced linearly (e.g., displaceable in the Y direction).

The projecting member 84 provided on the rolling switch 28 is inserted into the insertion hole 80 provided on the switch pedestal 78. In this case, the projecting member 84 is capable of being displaced in the A direction and the B direction inside the insertion hole 80.

The biasing member 70 elastically biases the rolling switch 28 toward a neutral position (the position shown in FIG. 7) in the movement range of the rolling switch 28 at all times. In a state in which the rolling switch 28 is not pressed in left and right directions, the rolling switch 28 is maintained in the neutral position under an elastic action of the biasing member 70.

The biasing member 70 is supported by a supporting projection 86 provided on the switch frame 68. The biasing member 70 of the present illustrated example is constituted by a torsion spring 70A. A coil part 88 of the torsion spring 70A is fixed to the supporting projection 86. A pair of arm members 90a, 90b of the torsion spring 70A extend from the coil part 88 to the operating element 82. A latching projection 87 disposed on the switch frame 68 is sandwiched between the pair of arm members 90a, 90b of the torsion spring 70A. In a state in which the rolling switch 28 is in the neutral position, a small gap (amount of play) exists between the rolling switch 28 and the pair of arm members 90a, 90b.

The movable-side terminal member 72 is fixed to the projecting member 84. The movable-side terminal member 72 of the present illustrated embodiment includes a base portion 93 fixed to the projecting member 84 by a fixing part 92 (a screw in the illustrated example), and a first contact portion 94 (movable-side contact portion) and a second contact portion 96 (movable-side contact portion), which are bent at substantially right angles at both ends of the base portion 93, and which extend toward the operating element 82 along the projecting member 84. As shown in FIG. 6, one end of the lead wire 91a is connected to a connection terminal 97 that extends out from the base portion 93. The other end of the lead wire 91a is connected to the handle-side terminal member 60c (see FIG. 3).

Between the projecting member 84 and the movable-side terminal member 72, a holder 98 is arranged for preventing the rolling switch 28 from being pulled out from the switch pedestal 78. By insertion of a positioning projection 85 disposed on the projecting member 84 into a positioning hole 99 provided on the holder 98, the holder 98 is positioned with respect to the projecting member 84. A portion of the holder 98 engages slidably in the A direction and the B direction on an arcuate lower surface 78d (see FIG. 7) disposed on a lower part of the switch pedestal 78.

The first fixed-side terminal member 74 and the second fixed-side terminal member 76 are fixed to the switch frame 68. The first fixed-side terminal member 74 of the present illustrated example includes a first fixed base portion 100, which is fixed to the switch frame 68 on one side relative to the projecting member 84, and a first contact plate 102 (first fixed-side contact portion), which is bent and extends out from the first fixed base portion 100 toward the rolling switch 28. The second fixed-side terminal member 76 of the present illustrated example includes a second fixed base portion 104, which is fixed to the switch frame 68 on another side relative to the projecting member 84, and a second contact plate 106 (second fixed-side contact portion), which is bent and extends out from the second fixed base portion 104 toward the rolling switch 28.

The respective fixed base portions 100, 104 are fixed to the switch frame 68 by fixing parts 108, 109 (screws in the illustrated example). The lead wire 91b is connected to a connection terminal 101 that extends out from the first fixed base portion 100 of the first fixed-side terminal member 74. The other end of the lead wire 91b is connected to the handle-side terminal member 60a. The lead wire 91c is connected to a connection terminal 105 (see FIG. 6) that extends out from the second fixed base portion 104 of the second fixed-side terminal member 76. The other end of the lead wire 91c is connected to the handle-side terminal member 60e.

As shown in FIG. 7, in the interior of the insertion hole 80, the first contact plate 102 faces the first contact portion 94 of the movable-side terminal member 72, and further is arranged so as to face an inner wall surface of a left side wall portion 78b on the switch pedestal 78 with a slight gap therebetween. Further, in the interior of the insertion hole 80, the second contact plate 106 faces the second contact portion 96 of the movable-side terminal member 72, and further is arranged so as to face an inner wall surface of a right side wall portion 78c on the switch pedestal 78 with a slight gap therebetween. Therefore, when pressed by the movable-side terminal member 72, the respective contact plates 102, 106 are elastically deformable over the gaps. Contact projections 103, 107, which project out on sides of the movable-side terminal member 72, are provided on the respective contact plates 102, 106.

The movable-side terminal member 72, the first fixed-side terminal member 74, and the second fixed-side terminal member 76 are constituted from a corrosion-resistant material, for example, stainless steel, titanium, a titanium alloy, etc. Alternatively, the movable-side terminal member 72, the first fixed-side terminal member 74, and the second fixed-side terminal member 76 may be constituted from conductive materials, and a conductive coating that exhibits corrosion resistance may be applied to at least the electrical contact portions (the first contact portion 94, the second contact portion 96, the first contact plate 102, the second contact plate 106) thereof. Examples of constituent materials for such a conductive coating include nickel, gold, silver, rhodium, chromium, and the like.

The manipulator 10A according to the present embodiment is constructed basically as described above. Next operations and advantages of the manipulator 10A will be described.

In the switch mechanism 66, which is constructed as described above, when the rolling switch 28 is positioned in the neutral position as shown in FIG. 7, the movable-side terminal member 72 is kept out of contact with either one of the first fixed-side terminal member 74 and the second fixed-side terminal member 76. Therefore, electricity is not conducted between the central handle-side terminal member 60c and the handle-side terminal member 60a on the left-hand side (see FIG. 3). Further, electricity is not conducted between the central handle-side terminal member 60c and the handle-side terminal member 60e on the right-hand side (see FIG. 3). Consequently, a rolling operation of the distal end working unit 18 is not carried out.

Figure 8:
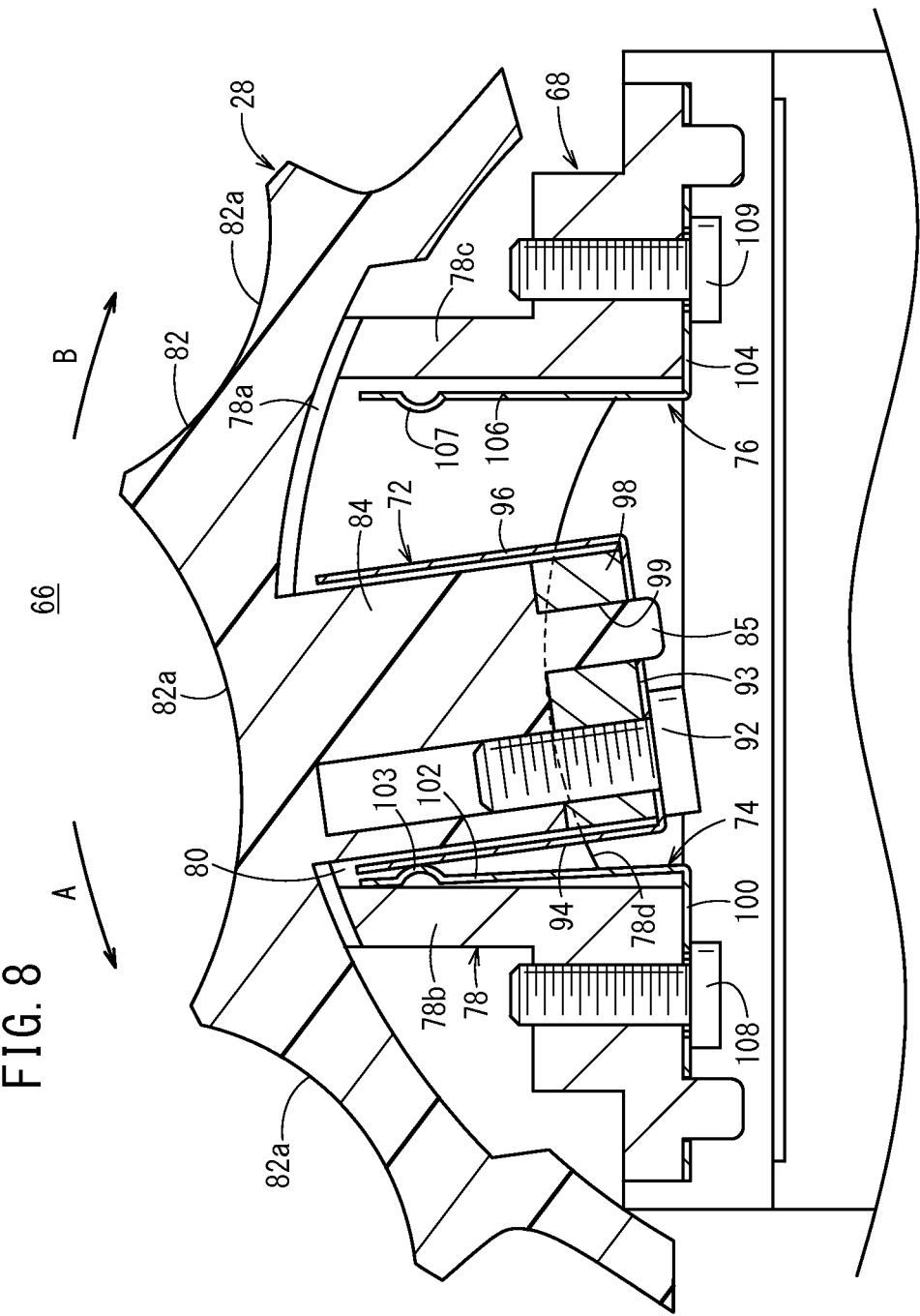
FIG. 8 is a cross-sectional view of the switch mechanism in a state in which a rolling switch is operated in an A direction.

As shown in FIG. 8, when the rolling switch 28 is operated and moved to the left (A direction) on the switch pedestal 78, the first contact portion 94 of the movable-side terminal member 72 and the first contact plate 102 of the first fixed-side terminal member 74 are placed in contact. Consequently, electricity is conducted between the central handle-side terminal member 60c and the handle-side terminal member 60a on the left-hand side (see FIG. 3), and conduction of electricity therebetween is detected by the controller 36 (see FIG. 1). As a result, the controller 36 controls driving of the motor 20, and in the distal end working unit 18, a left-handed rolling operation is carried out.

When the rolling switch 28 is operated and moved to the right (B direction) on the switch pedestal 78, the second contact portion 96 of the movable-side terminal member 72 and the second contact plate 106 of the second fixed-side terminal member 76 are placed in contact. Consequently, electricity is conducted between the central handle-side terminal member 60c and the handle-side terminal member 60e on the right-hand side (see FIG. 3), and conduction of electricity therebetween is detected by the controller 36. As a result, the controller 36 controls driving of the motor 20, and in the distal end working unit 18, a right-handed rolling operation is carried out.

In this case, according to the present embodiment, in the switch mechanism 66, the movable-side terminal member 72, the first fixed-side terminal member 74, and the second fixed-side terminal member 76 are constituted from a corrosion-resistant material. For this reason, even if the manipulator main body 11A is subjected to a sterilization treatment (autoclave sterilization, etc.) in which steam is used, it is unlikely for an oxide layer to be formed on the movable-side terminal member 72, the first fixed-side terminal member 74, and the second fixed-side terminal member 76, and conductivity therebetween can be maintained.

Further, when the first contact portion 94 of the movable-side terminal member 72 and the first contact plate 102 of the first fixed-side terminal member 74 come into contact, the first contact plate 102, as a result of being pressed by the first contact portion 94, is displaced slightly accompanying elastic deformation thereof. Along therewith, the first contact portion 94 and the first contact plate 102 are displaced relative to each other slightly in the surface direction of the first contact plate 102. Consequently, the first contact portion 94 and the first contact plate 102 slide while abutting against each other. More specifically, the first contact portion 94 and the first contact plate 102 rub against each other at the location of contact therebetween.

Further, similarly, when the second contact portion 96 of the movable-side terminal member 72 and the second contact plate 106 of the second fixed-side terminal member 76 come into contact, the second contact plate 106, as a result of being pressed by the second contact portion 96, is displaced slightly accompanying elastic deformation thereof. Along therewith, the second contact portion 96 and the second contact plate 106 are displaced relative to each other slightly in the surface direction of the second contact plate 106. Consequently, the second contact portion 96 and the second contact plate 106 slide while abutting against each other. More specifically, the second contact portion 96 and the second contact plate 106 rub against each other at the location of contact therebetween.

In this manner, accompanying operation of the rolling switch 28 that constitutes the switch operating member, at a time of contact between the movable-side terminal member 72, and the first fixed-side terminal member 74 or the second fixed-side terminal member 76, the first contact portion 94 and the first contact plate 102, or the second contact portion 96 and the second contact plate 106 rub against each other.

In addition, at the portions subjected to such mutual rubbing, an effect (refreshing effect) by which the electrical contact is activated can be obtained.

Consequently, for example, as a result of performing a sterilization treatment (autoclave sterilization, etc.) using steam with respect to the manipulator main body 11A, even if corrosion (an oxide layer) occurs in any one of the first contact portion 94, the second contact portion 96, the first contact plate 102, and the second contact plate 106 or even if foreign matter is deposited or adhered thereon, the electrical connection can suitably be assured due to the refreshing effect.

In the case of the present embodiment, when the first fixed-side terminal member 74 and the second fixed-side terminal member 76 come into contact respectively with the movable-side terminal member 72, contact regions thereof (the first contact plate 102, the second contact plate 106) with the movable-side terminal member 72 are displaced elastically. According to such a structure, when the first contact plate 102 or the second contact plate 106 is pressed by the movable-side terminal member 72 and then displaced elastically, mutual rubbing takes place at the contact regions. Thus, with a simple structure, the aforementioned refreshing effect can be obtained.

In the present embodiment, the first contact plate 102 and the second contact plate 106 are constituted as elastically deformable plate-shaped bodies. In this manner, in the first contact plate 102 and the second contact plate 106, since a spring element and an electrically conductive element are integrated into a single member, compared to such a spring element and such an electrically conductive element being constructed separately, the structure is simplified. Incidentally, in a modification of the first fixed-side terminal member 74 and the second fixed-side terminal member 76, the spring element and the electrically conductive element may be constituted separately. In this case, a structure is adopted in which the electrically conductive terminal part is supported elastically by an elastic member.

In this manner, with the switch mechanism 66, when the movable-side terminal member 72 and the first fixed-side terminal member 74 come into contact, the contact location (first contact plate 102) of the first fixed-side terminal member 74 with the movable-side terminal member 72 is constituted to be elastically displaceable. Further, when the movable-side terminal member 72 and the second fixed-side terminal member 76 come into contact, the contact location (second contact plate 106) of the second fixed-side terminal member 76 with the movable-side terminal member 72 is constituted to be elastically displaceable.

In contrast thereto, in a modification of the switch mechanism 66, when the movable-side terminal member 72 and the first fixed-side terminal member 74 come into contact, the contact location (first contact portion 94) of the movable-side terminal member 72 with the first fixed-side terminal member 74 may be constituted to be elastically displaceable. Further, when the movable-side terminal member 72 and the second fixed-side terminal member 76 come into contact, the contact location (second contact portion 96) of the movable-side terminal member 72 with the second fixed-side terminal member 76 may be constituted to be elastically displaceable. Configurations of this type can be realized by providing gaps between the first contact portion 94 and the projecting member 84, and between the second contact portion 96 and the projecting member 84. In accordance with such a configuration, when the movable-side terminal member 72 and the first fixed-side terminal member 74 come into contact, and when the movable-side terminal member 72 and the second fixed-side terminal member 76 come into contact, the respective contact locations thereof rub against each other, and the refreshing effect for electrical contact points is obtained.

In the case of the present embodiment, since the motor 20 (see FIG. 1), which serves as the drive source, is provided on the side of the drive unit 22, there is no need to provide electronic devices, which are susceptible to moisture, in the manipulator main body 11A. Accordingly, a sterilization treatment in which steam is used can suitably be performed on the manipulator main body 11A.

Figure 10:
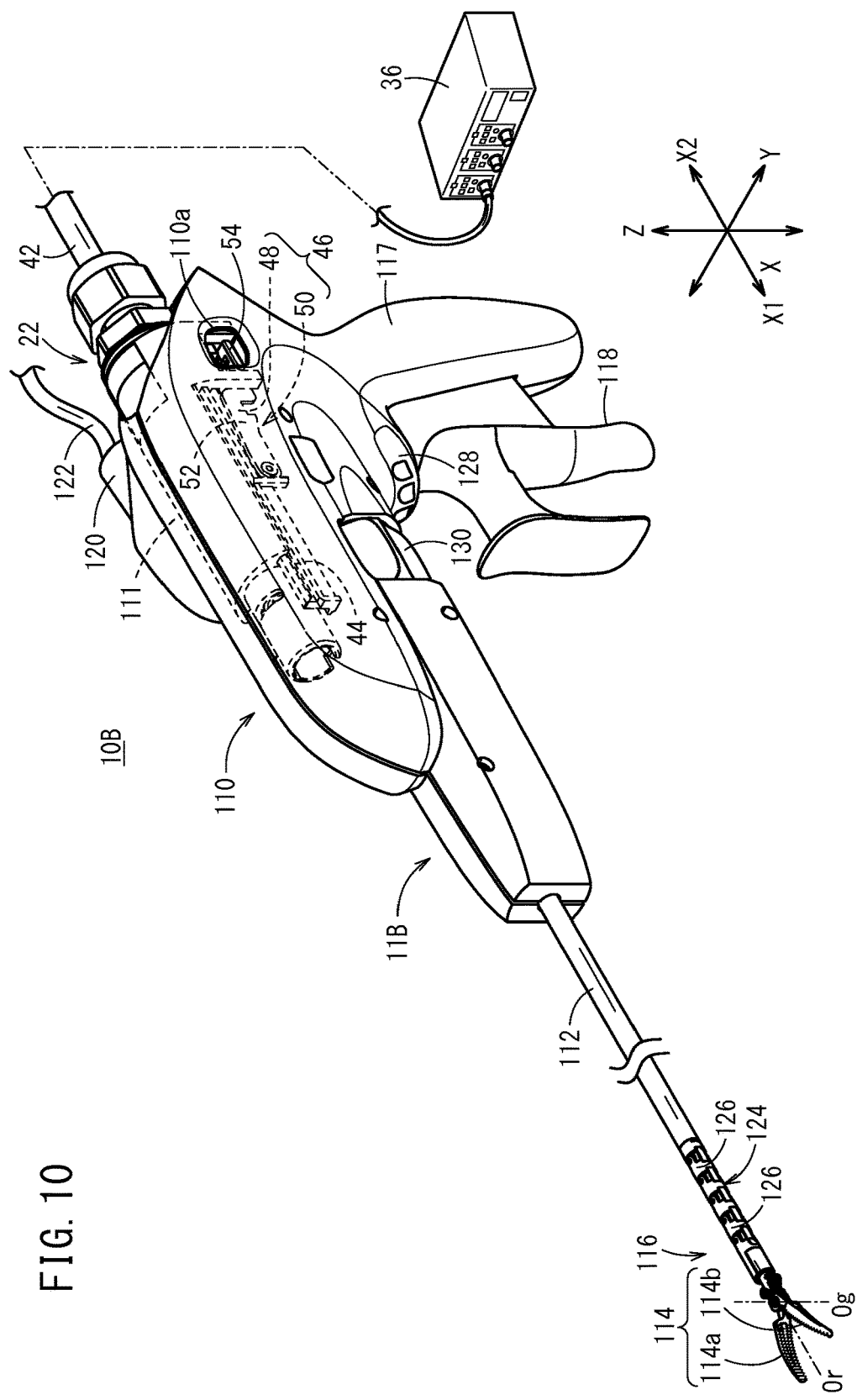
FIG. 10 is a perspective view of a medical manipulator according to another embodiment of the present invention.

The drive unit 22, which is constructed as described above, can be mounted and used not only with the manipulator main body 11A, which is constituted as a needle driver, but also with a manipulator main body 11B, which is constituted as an electrosurgical scalpel, as shown in FIG. 10. In this case, by combining together the manipulator main body 11B and the drive unit 22, an electrosurgical scalpel type medical manipulator 10B (hereinafter referred to in an abbreviated form as a "manipulator 10B"), which is driven by the motor 20, is constructed.

The manipulator main body 11B comprises a handle 110 on which a plurality of input operating members are provided, a shaft 112 that extends from the handle 110, and a distal end working unit 116 disposed on a distal end of the shaft 112 and including a gripper 114 (end effector).

The manipulator main body 11A shown in FIG. 1 is of an overall stick-like (rod-like) shape suitable for use as a needle driver. In contrast thereto, with the manipulator main body 11B shown in FIG. 10, a grip 117 that projects downwardly on a lower part of the handle 110 is provided, and the handle 110 is in the shape of a pistol as a whole, having a shape that is suitable for use as an electrosurgical scalpel. Further, such a pistol type handle shape also is suitable for use with scissors, a grasping implement, and a peeling implement, etc.

The gripper 114 is capable of making opening and closing movements, and serves as a portion for gripping biological tissue, and cauterizing the biological tissue by conduction of current through the tissue. The gripper 114 of the present illustrated example includes a first gripper member 114a and a second gripper member 114b, which are capable of swinging or pivoting in mutually opposite directions about an opening and closing operation axis Og.

The manipulator main body 11B may be constructed as a bipolar type of electrical scalpel in which the first gripper member 114a and the second gripper member 114b are electrically energized at different polarities, or a monopolar type of electrical scalpel in which either one of or both of the first gripper member 114a and the second gripper member 114b is electrically energized.

The opening and closing operation of the gripper 114 is carried out by mechanically transmitting the operation of a lever 118, which is provided on the handle 110, to the distal end working unit 116 through a non-illustrated opening/closing drive transmission system. More specifically, in the present illustrated example, the lever 118 is constructed as a manual operating member, and opening and closing operations of the gripper 114 are performed not by a motor drive, but by a manual drive on the basis of an operating force from the operator.

The lever 118 is disposed for displacement in forward and rearward directions with respect to the grip 117, such that when the lever 118 is pressed out forwardly relative to the grip 117, the gripper 114 opens, and when the lever 118 is drawn in rearwardly relative to the grip 117, the gripper 114 is closed. A structure may also be adopted in which the opening/closing operation of the gripper 114 is performed by a motor drive.

In the manipulator 10B in accordance with the combination of the manipulator main body 11B and the drive unit 22, a power supplying connector 120 is connected to the handle 110, whereby the manipulator 10B can be used as an electrosurgical scalpel. The power supplying connector 120 is connected to a non-illustrated high frequency power supply device through an energizing cable 122, and by the high frequency power supply device, a high frequency voltage is applied in order to electrically energize the gripper 114.

The distal end working unit 116 is capable of being tilted laterally (yaw operation) by a bending portion 124 disposed on a distal end of the shaft 112. The bending portion 124 has a plurality of joint members 126, which are coupled rotatably within a predetermined angular range to one another. Although in a state in which the joint members 126 are aligned coaxially, the bending portion 124 exhibits a linear shape, when the adjacent joint members 126 themselves are mutually tilted, the bending portion 124 exhibits a curved shape as a whole.

The tilting operation of the distal end working unit 116 is carried out by the controller 36 controlling driving of the motor 20 based on an operation made with respect to a tilting switch 128 (switch operating member) provided on the handle 110, and by mechanically transmitting the driving force of the motor 20 to the distal end working unit 116 through the handle 110 and the shaft 112. More specifically, in the present illustrated example, the tilting switch 128 is constructed as an electrical operating member, and the tilting operation of the distal end working unit 116 is performed by a motor drive.

The distal end working unit 116, at a portion thereof located more toward the distal end side than the bending portion 124, is capable of executing a rolling operation about the roll axis Or. The rolling operation is carried out by mechanically transmitting a rotating operation made with respect to a rotating knob 130 (input operating member), which is provided on the handle 110, to the distal end working unit 116 through a non-illustrated rolling drive transmission system. More specifically, in the present illustrated example, the rotating knob 130 is constructed as a manual operating member, and the rolling operation of the distal end working unit 116 is performed not by a motor drive, but by a manual drive on the basis of an operating force from the operator. A structure may also be adopted in which the rolling operation of the distal end working unit 116 is performed by a motor drive.

On an upper end side of the handle 110, a mounting hole 111 is provided, which opens rearwardly. The drive unit 22 is inserted into the mounting hole 111, and thus can be mounted with respect to the handle 110. More specifically, the drive unit 22 is capable of being attached to and detached from the proximal end side of the handle 110. In a state in which the drive unit 22 is mounted in the handle 110, so that operating tabs 54, which are disposed on the drive unit 22, can be touched and operated by the user, the operating tabs 54 protrude through openings 110a provided on side surfaces on left and right sides of the handle 110.

Similar to the handle 14 in the manipulator main body 11A, guide rails (not shown) are provided in the handle 110. Consequently, under a guiding action of the guide rails and the guide receiving members 44, the drive unit 22 can move smoothly relative to the handle 110, and the drive unit 22 can be mounted easily and reliably at an accurate positional relationship with respect to the handle 110.

Although omitted from illustration in FIG. 10, a driven coupling, which is capable of engaging with the drive coupling 40, is provided in the handle 110, as with the handle 14 in the manipulator main body 11A shown in FIG. 1. Consequently, in a state in which the drive unit 22 is mounted with respect to the handle 110, by engagement of the drive coupling 40 and the driven coupling, a driving force of the motor 20 can be transmitted reliably to the handle 110.

Although omitted from illustration in FIG. 10, handle-side terminal members 60 (see FIG. 3) are provided in the handle 110, which are similar to those of the handle 14 in the manipulator main body 11A shown in FIG. 1. In a state in which the drive unit 22 is attached to the handle 110, the handle-side terminal members 60 and the unit-side terminal members 62 (see FIG. 4) provided on the drive unit 22 are placed in contact. According to this structure, the operating state of the tilting switch 128 can be detected by the controller 36, and the controller 36 can appropriately control driving of the motor 20.

On the handle 110, similar to the handle 14 of the manipulator main body 11A shown in FIG. 1, an engagement member 48 is provided that is capable of engaging with the lever member 52 disposed on the drive unit 22. Accordingly, together with attachment of the drive unit 22 with respect to the handle 110, a condition (locked state) is brought about in which movement of the drive unit 22 in the proximal end direction relative to the handle 110 is prevented.

In the foregoing manner, with the manipulators 10A, 10B, the drive unit 22 can easily and reliably be attached with respect to the handles 14, 110 having different functions and shapes. Further, based on an operation of an input operating member (rolling switch 28, tilting switch 128) disposed on the handles 14, 110, the motor 20 can be driven, and the distal end working unit 116 can be operated by the driving force thereof.

The form of the manipulator main bodies 11A, 11B, which enable attachment and detachment of the drive unit 22, is not limited to the two forms (needle driver, electrosurgical scalpel) described above, and forms having other different functions and shapes, for example, scissors, a grasping forceps, or the like, may be provided. In addition, a suction device, a cleaning device, an energy device, etc., may be provided.

Figure 11:
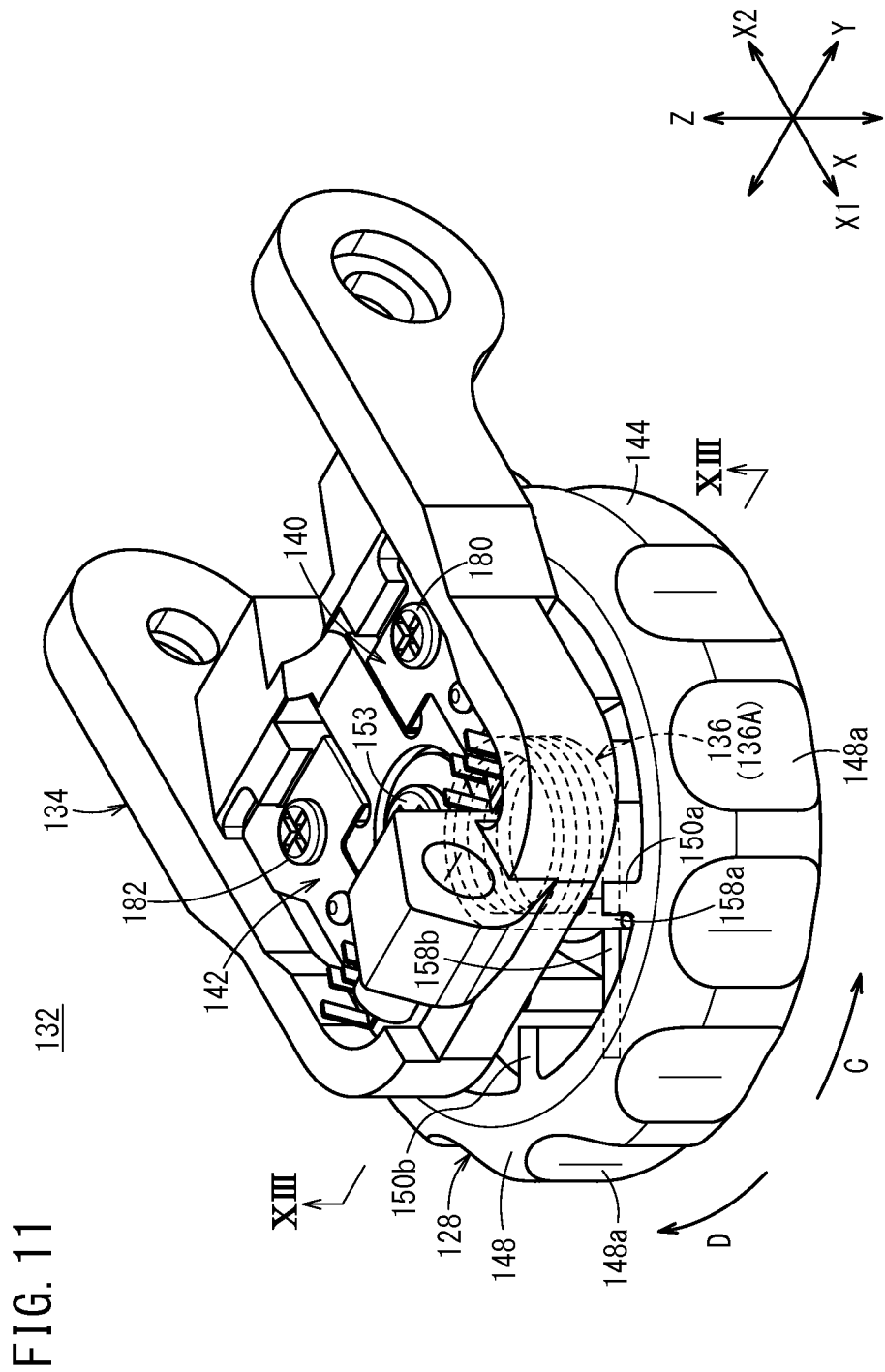
FIG. 11 is a perspective view of a switch mechanism of the medical manipulator illustrated in FIG. 10.
Figure 12:
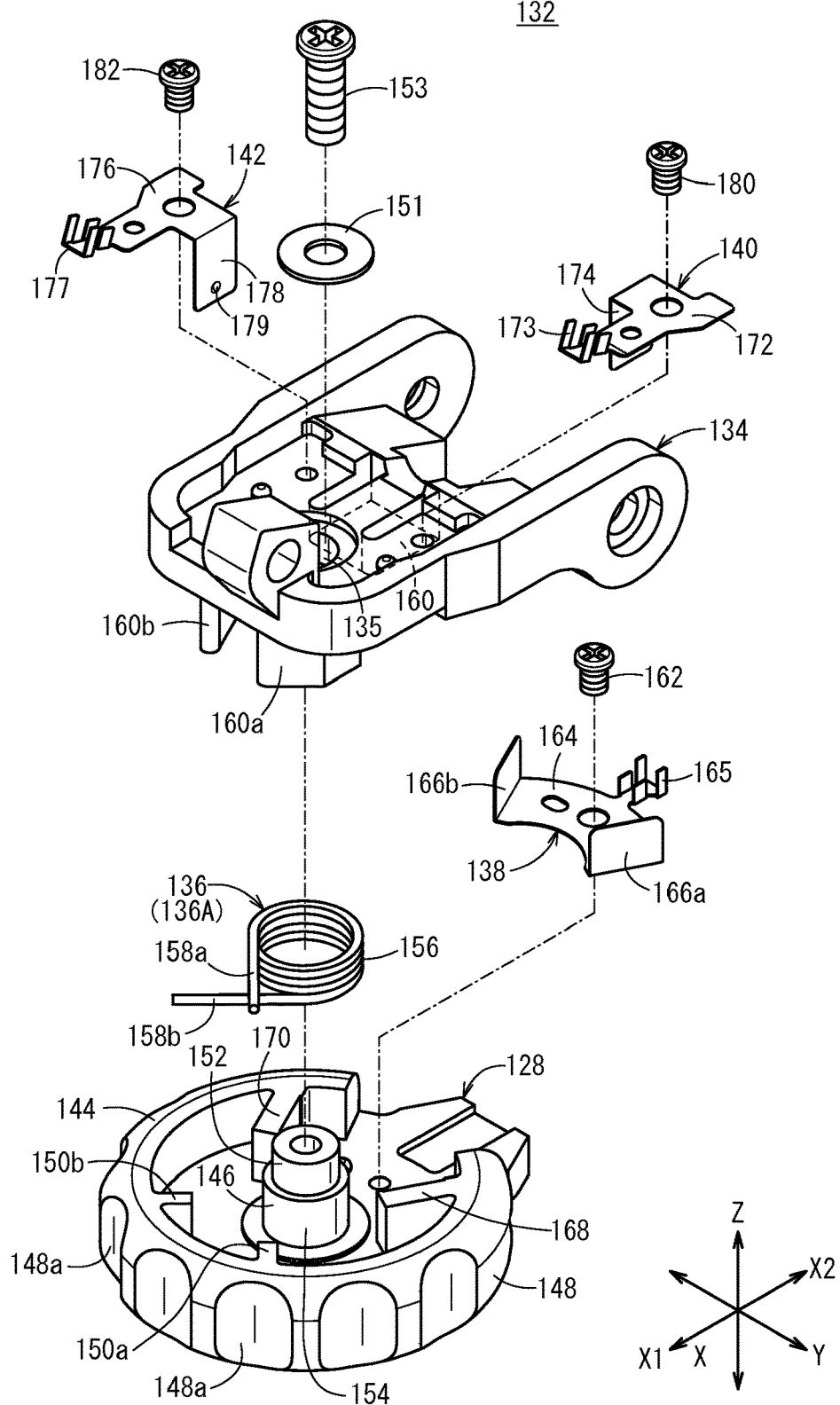
FIG. 12 is an exploded perspective view of the switch mechanism shown in FIG. 11.
Figure 13:
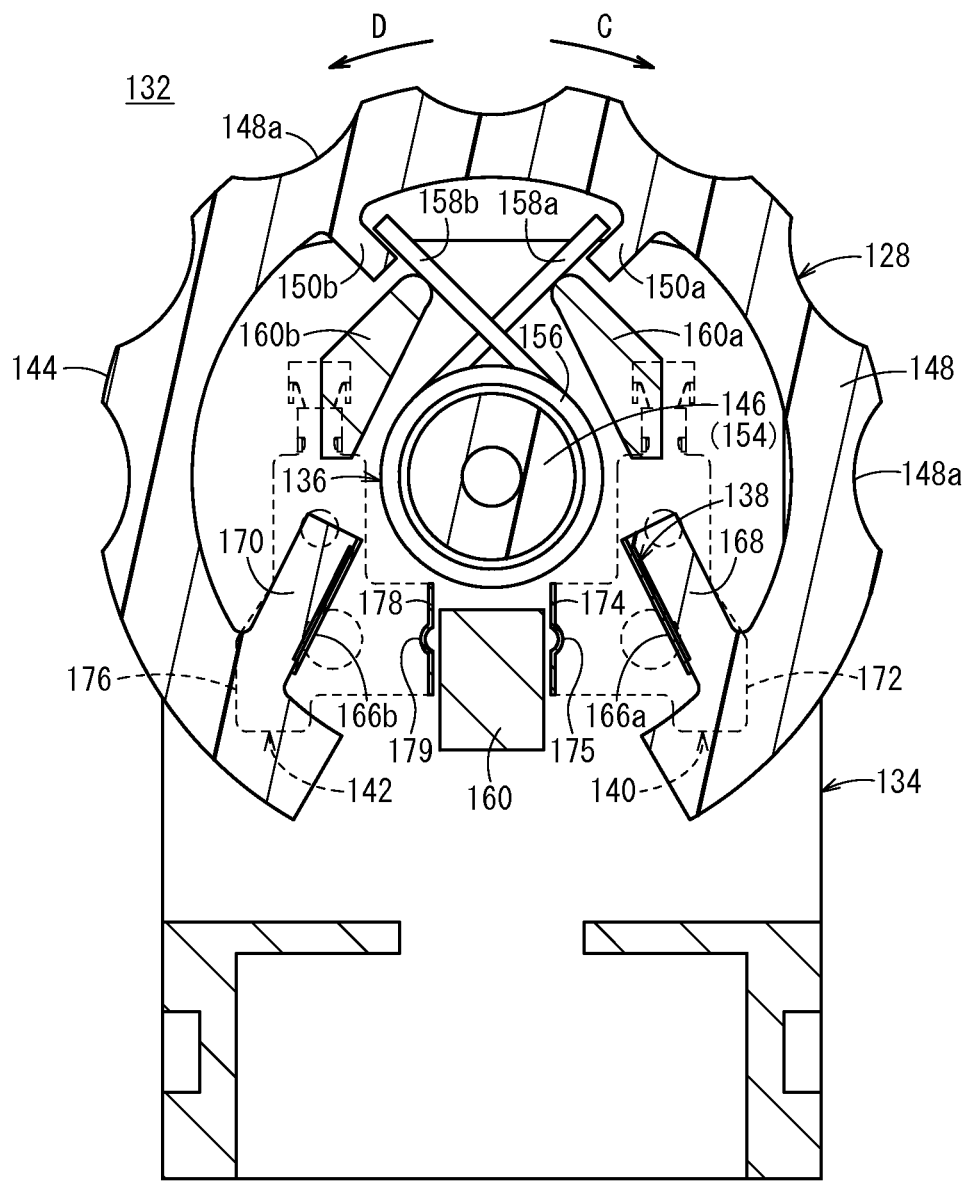
FIG. 13 is a cross-sectional view of the switch mechanism taken along line XIII-XIII of FIG. 11.

FIG. 11 is a perspective view showing a switch mechanism 132 including a tilting switch 128. FIG. 12 is an exploded perspective view of the switch mechanism 132. FIG. 13 is a cross-sectional view of the switch mechanism 132 taken along line XIII-XIII of FIG. 11. As shown in FIGS. 11 through 13, the switch mechanism 132 includes a switch frame 134, the tilting switch 128 that makes up the switch operating member, a biasing member 136, a movable-side terminal member 138, a first fixed-side terminal member 140, and a second fixed-side terminal member 142.

The switch frame 134 is fixed to a non-illustrated frame disposed in the interior of a casing of the handle 110. A support hole 135 is formed to penetrate in the thickness direction of the switch frame 134.

The tilting switch 128 is a portion that is operated by a finger of the user of the manipulator 10B. The tilting switch 128 of the present illustrated example includes an operating element 144 that is constituted in a substantially circular shape, and a projecting member 146 that projects from the operating element 144. Further, a circumferential side wall portion 148 that extends in a circumferential direction is disposed on the operating element 144. On an outer circumferential part of the circumferential side wall portion 148, a plurality of arcuate recesses 148a are provided to which the finger can easily be applied. Inwardly projecting engagement projections 150a, 150b are disposed on an inner circumferential part of the circumferential side wall portion 148.

A distal end side portion of the projecting member 146 is constituted as a cylindrically shaped switch shaft 152. The switch shaft 152 is inserted into the support hole 135. By this feature, the tilting switch 128 is supported pivotally about the center of the switch shaft 152 with respect to the switch frame 134. Further, in a modification of the tilting switch 128, the tilting switch 128 may be disposed swingably by an arcuately shaped slide surface. Alternatively, according to another modification of the tilting switch 128, the tilting switch 128 may be arranged so as to be displaced linearly (e.g., displaceable in the Y direction).

A fixing part 153 (a screw in the illustrated example) is fixed to the switch shaft 152 through a washer 151, and thereby, the tilting switch 128 is prevented from being pulled off from the switch frame 134.

A biasing member 136 elastically biases the tilting switch 128 toward a neutral position (the position shown in FIG. 13) in the movement range of the tilting switch 128 at all times. In a state in which the tilting switch 128 is not pressed in left and right directions, the tilting switch 128 is maintained in the neutral position under an elastic action of the biasing member 136.

The biasing member 136 is supported by a projecting member 146 provided on the tilting switch 128. The biasing member 136 of the present illustrated example is constituted by a torsion spring 136A. A root portion 154 of the projecting member 146 is inserted into a coil part 156 of the torsion spring 136A. A pair of arm members 158a, 158b of the torsion spring 136A extend from the coil part 156 to a circumferential side wall portion 148 of the tilting switch 128, and intersect each other as viewed in plan.

In a state in which the tilting switch 128 is in the neutral position, the pair of arm members 158a, 158b of the torsion spring 136A are caught on latching projections 160a, 160b, which are provided on the switch frame 134. As shown in FIG. 13, in a state in which the tilting switch 128 is in the neutral position, a small gap (amount of play) exists between the engagement projections 150a, 150b and the pair of arm members 158a, 158b.

The movable-side terminal member 138 is fixed to the tilting switch 128. As shown in FIG. 12, the movable-side terminal member 138 of the present illustrated embodiment includes an arcuate base portion 164 fixed to the tilting switch 128 by a fixing part 162 (a screw in the illustrated example), and a first contact portion 166a (movable-side contact portion) and a second contact portion 166b (movable-side contact portion), which are bent at substantially right angles at both ends of the base portion 164, and which extend toward the switch frame 134.

In the first contact portion 166a, an opposite side thereof from a side in contact with the first fixed-side terminal member 140 is supported by a contact support member 168 provided on the switch frame 134. In the second contact portion 166b, an opposite side thereof from a side in contact with the second fixed-side terminal member 142 is supported by a contact support member 170 provided on the switch frame 134.

As shown in FIG. 12, a connection terminal 165 projects out from the base portion 164. Similar to the handle 14 in the manipulator main body 11A, lead wires 91a to 91c (see FIG. 3) are provided in the handle 110. The connection terminal 165 is connected through the lead wire 91a (see FIG. 3) to the handle-side terminal member 60c (see FIG. 3).

The first fixed-side terminal member 140 and the second fixed-side terminal member 142 are fixed to the switch frame 134. The first fixed-side terminal member 140 of the present illustrated example includes a first fixed base portion 172, which is fixed to the switch frame 134 on one side in the lateral direction (Y direction), and a first contact plate 174 (first fixed-side contact portion), which is bent and extends out from the first fixed base portion 172 toward the tilting switch 128. The second fixed-side terminal member 142 of the present illustrated example includes a second fixed base portion 176, which is fixed to the switch frame 134 on another side in the lateral direction (Y direction), and a second contact plate 178 (second fixed-side contact portion), which is bent and extends out from the second fixed base portion 176 toward the tilting switch 128.

The respective fixed base portions 172, 176 are fixed to the switch frame 134 by fixing parts 180, 182 (screws in the illustrated example). A connection terminal 173 that extends out from the first fixed base portion 172 of the first fixed-side terminal member 140 is connected through the lead wire 91b to the handle-side terminal member 60a (see FIG. 3). A connection terminal 177 that extends out from the second fixed base portion 176 of the second fixed-side terminal member 142 is connected through the lead wire 91c to the handle-side terminal member 60e (see FIG. 3).

As shown in FIG. 12, the first contact plate 174 faces the first contact portion 166a of the movable-side terminal member 138, and further is arranged so as to face a wall portion 160 provided on the switch frame 134 with a slight gap therebetween. The second contact plate 178 faces the second contact portion 166b of the movable-side terminal member 138, and further is arranged so as to face the wall portion 160 with a slight gap therebetween. Therefore, when pressed by the movable-side terminal member 138, the respective contact plates 174, 178 are elastically deformable over the gaps. Contact projections 175, 179, which project out toward the movable-side terminal member 138, are provided on the respective contact plates 174, 178.

The movable-side terminal member 138, the first fixed-side terminal member 140, and the second fixed-side terminal member 142 are constituted from a corrosion-resistant material, for example, stainless steel, titanium, a titanium alloy, etc. Alternatively, the movable-side terminal member 138, the first fixed-side terminal member 140, and the second fixed-side terminal member 142 may be constituted by conductive materials, and a conductive coating that exhibits corrosion resistance may be applied to at least the electrical contact portions (the first contact portion 166a, the second contact portion 166b, the first contact plate 174, the second contact plate 178) thereof. Examples of constituent materials for such a conductive coating include nickel, gold, silver, rhodium, chromium, and the like.

As shown in FIG. 13, when the tilting switch 128 is positioned in the neutral position, the movable-side terminal member 138 is kept out of contact with either one of the first fixed-side terminal member 140 and the second fixed-side terminal member 142. Therefore, electricity is not conducted between the central handle-side terminal member 60c and the handle-side terminal member 60a on the left-hand side (see FIG. 3). Further, electricity is not conducted between the central handle-side terminal member 60c and the handle-side terminal member 60e on the right-hand side (see FIG. 3). Consequently, a tilting operation (yaw operation) of the distal end working unit 116 is not carried out.

In the switch mechanism 132, which is constructed as described above, as shown in FIG. 14, when the tilting switch 128 is operated and moved in the C direction, the first contact portion 166a of the movable-side terminal member 138 and the first contact plate 174 of the first fixed-side terminal member 140 are placed in contact. Consequently, electricity is conducted between the central handle-side terminal member 60c and the handle-side terminal member 60a on the left-hand side (see FIG. 3), and conduction of electricity therebetween is detected by the controller 36 (see FIG. 10). As a result, the controller 36 controls driving of the motor 20, and in the distal end working unit 116, a left-handed tilting operation (yaw operation) is carried out.

Figure 14:
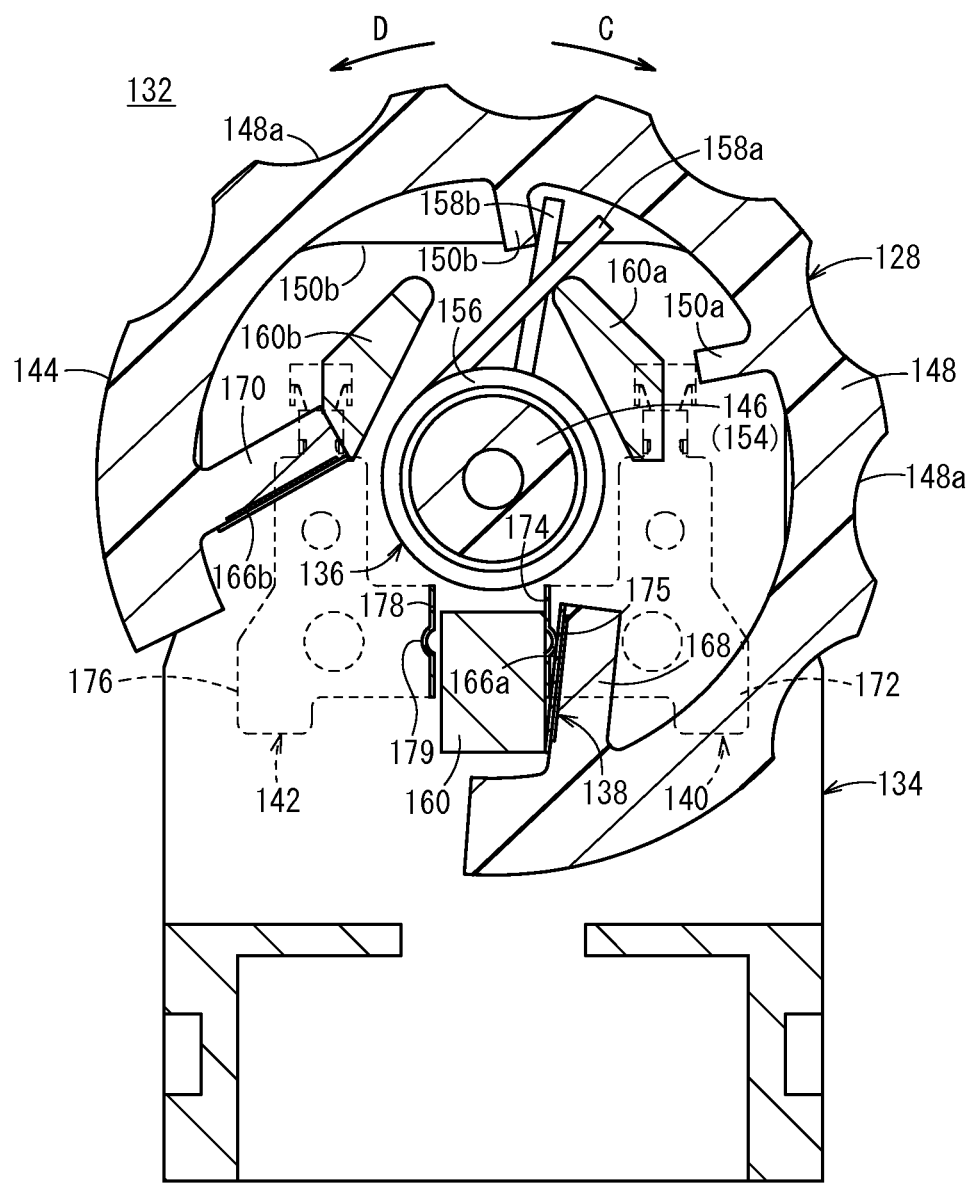
FIG. 14 is a cross-sectional view of the switch mechanism in a state in which a tilting switch is operated in a C direction.

Conversely to FIG. 14, when the tilting switch 128 is operated and moved in the D direction, the second contact portion 166b of the movable-side terminal member 138 and the second contact plate 178 of the second fixed-side terminal member 142 are placed in contact. Consequently, electricity is conducted between the central handle-side terminal member 60c and the handle-side terminal member 60e on the right-hand side (see FIG. 3), and conduction of electricity therebetween is detected by the controller 36. As a result, the controller 36 controls driving of the motor 20, and in the distal end working unit 116, a right-handed tilting operation (yaw operation) is carried out.

In this case, in the switch mechanism 132, the movable-side terminal member 138, the first fixed-side terminal member 140, and the second fixed-side terminal member 142 are constituted from a corrosion-resistant material. For this reason, even if the manipulator main body 11B is subjected to a sterilization treatment (autoclave sterilization, etc.) in which steam is used, it is unlikely for an oxide layer to be formed on the movable-side terminal member 138, the first fixed-side terminal member 140, and the second fixed-side terminal member 142, and conductivity therebetween can be maintained.

Further, when the first contact portion 166a of the movable-side terminal member 138 and the first contact plate 174 of the first fixed-side terminal member 140 come into contact, the first contact plate 174, as a result of being pressed by the first contact portion 166a, is displaced slightly accompanying elastic deformation thereof. Along therewith, the first contact portion 166a and the first contact plate 174 are displaced relative to each other slightly in the surface direction of the first contact plate 174. Consequently, the first contact portion 166a and the first contact plate 174 slide while abutting against each other. More specifically, the first contact portion 166a and the first contact plate 174 rub against each other at the location of contact therebetween.

Further, similarly, when the second contact portion 166b of the movable-side terminal member 138 and the second contact plate 178 of the second fixed-side terminal member 142 come into contact, the second contact plate 178, as a result of being pressed by the second contact portion 166b, is displaced slightly accompanying elastic deformation thereof. Along therewith, the second contact portion 166b and the second contact plate 178 are displaced relative to each other slightly in the surface direction of the second contact plate 178. Consequently, the second contact portion 166b and the second contact plate 178 slide while abutting against each other. More specifically, the second contact portion 166b and the second contact plate 178 rub against each other at the location of contact therebetween.

In this manner, when the tilting switch 128 is operated to thereby bring the movable-side terminal member 138 into contact with the first fixed-side terminal member 140 or the second fixed-side terminal member 142, the first contact portion 166a and the first contact plate 174, or the second contact portion 166b and the second contact plate 178 rub against each other. In addition, at the portions subjected to such mutual rubbing, an effect (refreshing effect) by which the electrical contact is activated can be obtained.

Consequently, for example, even if the manipulator main body 11B is subjected to a sterilization treatment (autoclave sterilization, etc.) using steam, whereby corrosion (an oxide layer) in any one of the first contact portion 166a, the second contact portion 166b, the first contact plate 174, and the second contact plate 178 occurs or whereby foreign matter is deposited or adhered thereon, the electrical connection can suitably be assured as a result of the refreshing effect.

With the switch mechanism 132, when the first fixed-side terminal member 140 and the second fixed-side terminal member 142 come into contact respectively with the movable-side terminal member 138, contact regions thereof (the first contact plate 174, the second contact plate 178) with the movable-side terminal member 138 are displaced elastically. According to such a structure, when the first fixed-side terminal member 140 or the second fixed-side terminal member 142 is displaced elastically as a result of being pressed by the movable-side contact portions, mutual rubbing takes place at the contact regions. Thus, with a simple structure, the aforementioned refreshing effect can be obtained.

In the switch mechanism 132, the first contact plate 174 and the second contact plate 178 are constituted as elastically deformable plate-shaped bodies. In this manner, in the first contact plate 174 and the second contact plate 178, since the spring element and the electrically conductive element thereof are integrated as a single member, compared to the spring element and the electrically conductive element being constructed separately, the structure is simplified.

In this manner, with the switch mechanism 132, when the movable-side terminal member 138 and the first fixed-side terminal member 140 come into contact, the contact location (first contact plate 174) of the first fixed-side terminal member 140 with the movable-side terminal member 138 is constituted to be elastically displaceable. Further, when the movable-side terminal member 138 and the second fixed-side terminal member 142 come into contact, the contact location (second contact plate 178) of the second fixed-side terminal member 142 with the movable-side terminal member 138 is constituted to be elastically displaceable.

In contrast thereto, in a modification of the switch mechanism 132, when the movable-side terminal member 138 and the first fixed-side terminal member 140 come into contact, the contact location (first contact portion 166a) of the movable-side terminal member 138 with the first fixed-side terminal member 140 may be constituted to be elastically displaceable. Further, when the movable-side terminal member 138 and the second fixed-side terminal member 142 come into contact, the contact location (second contact portion 166b) of the movable-side terminal member 138 with the second fixed-side terminal member 142 may be constituted to be elastically displaceable. Configurations of this type can be realized by providing gaps respectively between the first contact portion 166a and the contact support member 168, and between the second contact portion 166b and the contact support member 170. In accordance with such a configuration, when the movable-side terminal member 138 and the first fixed-side terminal member 140 come into contact, and when the movable-side terminal member 138 and the second fixed-side terminal member 142 come into contact, the respective contact locations thereof rub against each other, and the refreshing effect is obtained.

Figure 15A:
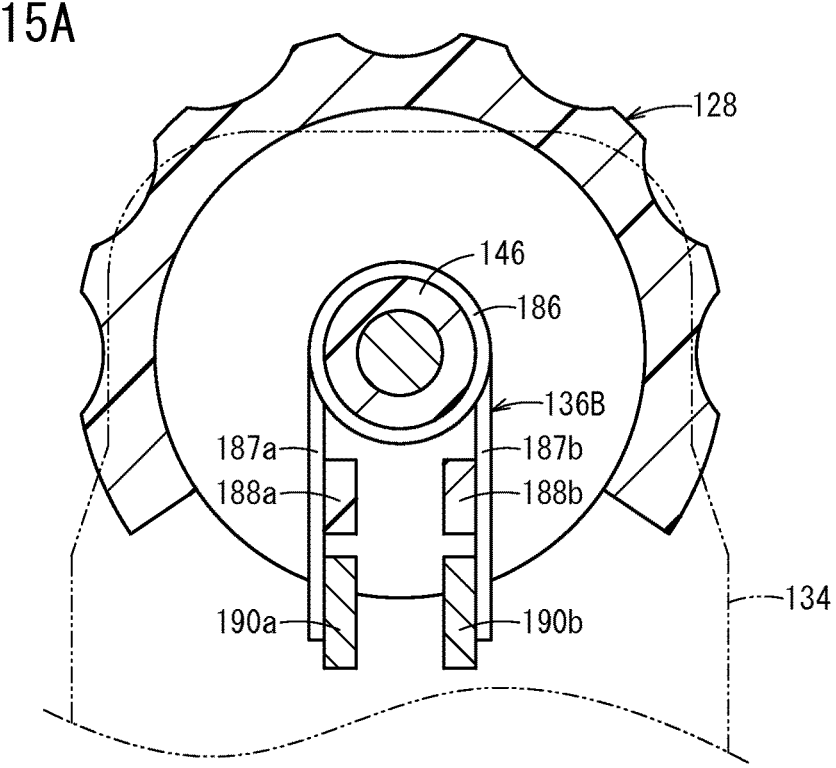
FIG. 15A is a view showing another structural example for returning the tilting switch to a neutral position.
Figure 15B:
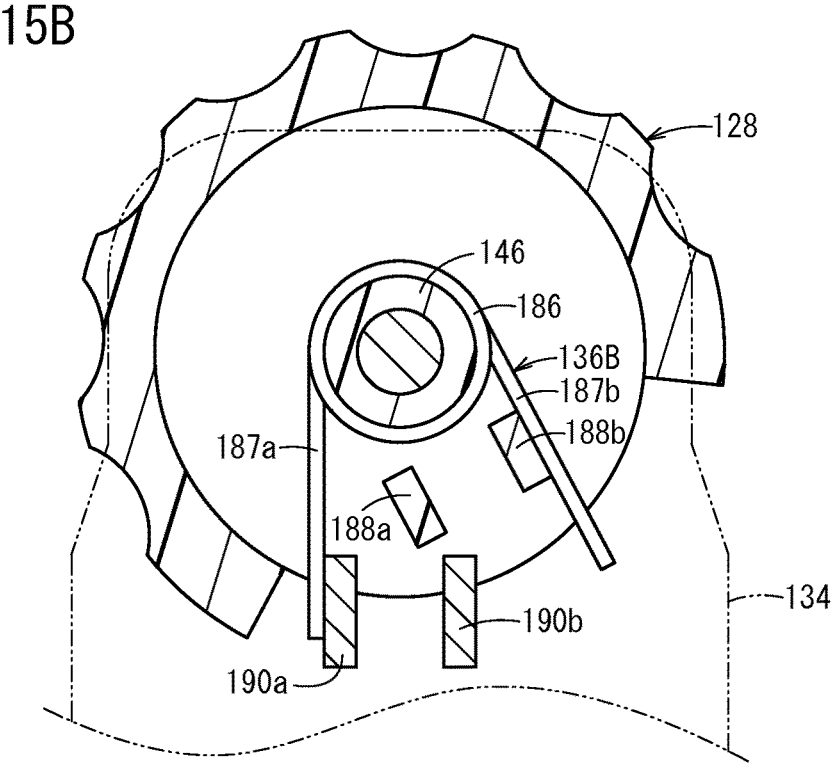
FIG. 15B is a view showing a condition in which the tilting switch shown in FIG. 15A has been operated.

FIGS. 15A and 15B are views showing another structural example for returning the tilting switch 128 to the neutral position. In FIGS. 15A and 15B, the movable-side terminal member 138, the first fixed-side terminal member 140, and the second fixed-side terminal member 142 are omitted from illustration.

In FIG. 15A, the coil part 156 of the torsion spring 136B is supported by the projecting member 146 of the tilting switch 128. A pair of engagement projections 188a, 188b are disposed on the tilting switch 128. Without intersecting each other as viewed in plan, a pair of arms 187a, 187b of the torsion spring 136B are caught respectively on the engagement projections 188a, 188b, from outer sides of the pair of engagement projections 188a, 18b.

Distal end sides of the pair of arms 187a, 187b are capable of engaging with latching projections 190a, 190b provided on the side of the switch frame 134. By the pair of arms 187a, 187b being engaged with the latching projections 190a, 190b, the biasing member 136 elastically biases the tilting switch 128 toward a neutral position in the movement range of the tilting switch 128 at all times. Accordingly, as shown in FIG. 15A, in a state in which the tilting switch 128 is not rotationally operated, the tilting switch 128 is maintained in the neutral position under an elastic action of the biasing member 136.

When the tilting switch 128 is rotationally operated in one direction from the neutral position, as shown in FIG. 15B, although one of the arms 187a is latched by the latching projection 190a and thus is not displaced, the other arm 187b is pressed by the other engagement projection 188b, and is displaced in the same direction as the direction of rotation of the tilting switch 128. In the state shown in FIG. 15B, upon separating the finger of the operator away from the tilting switch 128, based on an elastic restorative force of the torsion spring 136B, the arm 187b presses the other engagement projection 188b, whereupon the tilting switch 128 is rotated. As a result, the tilting switch 128 is restored to the neutral position shown in FIG. 15A. Also if the tilting switch 128 is rotationally operated in a direction opposite to that shown in FIG. 15B, in a similar manner, upon separating the finger away from the tilting switch 128, by the elastic restorative force of the biasing member 136, the tilting switch 128 is restored to the neutral position.

Although certain preferred embodiments of the present invention have been shown and described in detail above, it should be understood that various changes and modifications may be made to the embodiments without departing from the scope of the invention as set forth in the appended claims.

What is claimed is:

1. A medical manipulator equipped with a switch mechanism, the switch mechanism comprising:
   a movable switch operating member;
   a switch frame having a pedestal with a slide surface, the slide surface supporting the movable switch operating member;
   a movable-side contact portion disposed on the switch operating member; and
   a fixed-side contact portion, which is capable of contacting the movable-side contact portion to make an electrical connection;

the movable-side contact portion being adapted to abut against the fixed-side contact portion when the movable switch operating member is operated, the movable-side contact portion being biased toward a neutral position so that the movable-side contact portion is not in contact with the fixed-side contact portion;

wherein at least electrical contact portions of the movable-side contact portion and the fixed-side contact portion are formed from a corrosion-resistant material; and wherein the movable switch operating member has a projecting member which extends through an insertion hole in the pedestal, the movable-side contact portion being disposed on the projecting member.

2. The medical manipulator according to claim 1, wherein at a time of contact, the movable-side contact portion and the fixed-side contact portion slide against each other such that the electrical contact portions of the movable-side contact portion and the fixed-side contact portion rub against one another.

3. The medical manipulator according to claim 2, wherein when the fixed-side contact portion comes into contact with the movable-side contact portion, a contact region of the fixed-side contact portion with the movable-side contact portion is capable of being displaced elastically.

4. The medical manipulator according to claim 3, wherein the fixed-side contact portion is an elastically deformable plate-shaped body.

5. The medical manipulator according to claim 2, wherein when the movable-side contact portion comes into contact with the fixed-side contact portion, a contact region of the movable-side contact portion with the fixed-side contact portion is capable of being displaced elastically.

6. The medical manipulator according to claim 5, wherein the movable-side contact portion is an elastically deformable plate-shaped body.

7. The medical manipulator according to claim 1, wherein the fixed-side contact portion comprises:
a first fixed-side contact portion that abuts against the movable-side contact portion when the switch operating member is operated in a first direction from the neutral position; and
a second fixed-side contact portion that abuts against the movable-side contact portion when the switch operating member is operated in a second direction opposite to the first direction from the neutral position.

8. The medical manipulator according to claim 1, further comprising:
a main body including a handle; and
a drive unit configured to releaseably attach to the handle, the drive unit including a drive source,
wherein the switch mechanism is disposed in the handle.

9. The medical manipulator according to claim 1, wherein the slide surface has an arcuate shape.

10. The medical manipulator according to claim 1, wherein the switch mechanism comprises a biasing member which biases the movable-side contact portion toward the neutral position, the biasing member being fixed to a supporting projection that is provided on the switch frame.

11. The medical manipulator according to claim 1, wherein the fixed-side contact portion has a base attached to the switch frame.

12. The medical manipulator according to claim 11, wherein the electrical contact portion of the fixed-side contact portion extends from the base at an angle relative to the base.

13. A medical manipulator equipped with a switch mechanism, the switch mechanism comprising:
a movable switch operating member;
a movable-side contact portion disposed on the switch operating member; and
a fixed-side contact portion, which is capable of contacting the movable-side contact portion to make an electrical connection;
the movable-side contact portion being adapted to abut against the fixed-side contact portion when the movable switch operating member is operated, the movable-side contact portion being biased toward a neutral position so that the movable-side contact portion is not in contact with the fixed-side contact portion;
wherein at least electrical contact portions of the movable-side contact portion and the fixed-side contact portion are formed from a corrosion-resistant material; and
wherein the switch mechanism comprises a switch frame and a rotating shaft disposed on the switch frame, the rotating shaft supporting the movable switch operating member.

14. A medical manipulator equipped with a switch mechanism, the switch mechanism comprising:
a movable switch operating member;
a switch frame having a support hole;
a movable-side contact portion disposed on the switch operating member; and
a fixed-side contact portion, which is capable of contacting the movable-side contact portion to make an electrical connection;
the movable-side contact portion being adapted to abut against the fixed-side contact portion when the movable switch operating member is operated, the movable-side contact portion being biased toward a neutral position so that the movable-side contact portion is not in contact with the fixed-side contact portion;
wherein at least electrical contact portions of the movable-side contact portion and the fixed-side contact portion are formed from a corrosion-resistant material;
wherein the movable switch operating member comprises a projecting member, which is inserted into the support hole of the switch frame, the projecting member pivotally supporting the movable switch operating member relative to the switch frame; and
wherein the switch mechanism comprises a biasing member which biases the movable-side contact portion toward the neutral position, the biasing member being disposed on and around a circumference of the projecting member of the movable switch operating member.

15. The medical manipulator according to claim 14, wherein the biasing member has two arms, and wherein in the neutral position, each arm contacts one of two latching projections provided on the switch frame.

16. The medical manipulator according to claim 14, wherein:
the movable-side contact portion is attached to the movable switch operating member,
the fixed-side contact portion has a base attached to one side of the switch frame, and
the electrical contact portion of the fixed-side contact portion extends from the base at an angle relative to the base and extends through the switch frame toward the movable switch operating member.

* * * * *